US 9,241,748 B2

(12) United States Patent
Bernstein et al.

(10) Patent No.: US 9,241,748 B2
(45) Date of Patent: Jan. 26, 2016

(54) SYSTEM FOR BINDING BONE

(71) Applicant: ACUTE Innovations LLC, Hillsboro, OR (US)

(72) Inventors: Oren S. Bernstein, Portland, OR (US); Joel Gillard, Portland, OR (US); Sara Russi, Portland, OR (US); Andrew W. Seykora, Portland, OR (US); Mariah Knight, Hillsboro, OR (US)

(73) Assignee: Acute Innovations LLC, Hillsboro, OR (US)

( * ) Notice: Subject to any disclaimer, the term of this patent is extended or adjusted under 35 U.S.C. 154(b) by 251 days.

(21) Appl. No.: 13/874,171

(22) Filed: Apr. 30, 2013

(65) Prior Publication Data
US 2013/0289564 A1 Oct. 31, 2013

Related U.S. Application Data

(60) Provisional application No. 61/640,486, filed on Apr. 30, 2012, provisional application No. 61/641,703, filed on May 2, 2012.

(51) Int. Cl.
*A61B 17/82* (2006.01)
*A61B 17/88* (2006.01)

(52) U.S. Cl.
CPC ............ *A61B 17/82* (2013.01); *A61B 17/823* (2013.01); *A61B 17/8861* (2013.01)

(58) Field of Classification Search
CPC .... A61B 17/82; A61B 17/823; A61B 17/826; A61B 17/8861; Y10T 24/3916; Y10T 24/3918; Y10T 24/3924; Y10T 24/3933
See application file for complete search history.

(56) References Cited

U.S. PATENT DOCUMENTS

| | | | |
|---|---|---|---|
| 76,141 A | 3/1868 | Barnum | |
| 190,641 A | 5/1877 | Stouffer | |
| 866,144 A | 9/1907 | Kobert | |
| 2,171,524 A | 9/1939 | Gates | |
| 2,276,571 A | 3/1942 | Grypma | |
| 2,452,098 A * | 10/1948 | Brooks | ........................... 40/662 |
| 2,464,432 A | 3/1949 | Brickman | |
| 2,903,772 A * | 9/1959 | McKinlay | .................. 24/129 R |
| 2,986,787 A | 6/1961 | Ackermann | |

(Continued)

FOREIGN PATENT DOCUMENTS

| EP | 1080693 A1 | 3/2001 |
|---|---|---|
| EP | 2367489 A | 9/2011 |

(Continued)

OTHER PUBLICATIONS

Synthes® (USA), Modular Sternal Cable System brochure (2004); 15 pages.

(Continued)

*Primary Examiner* — Anu Ramana
(74) *Attorney, Agent, or Firm* — Kolisch Hartwell, P.C.

(57) ABSTRACT

System, including methods, apparatus, and kits for binding bone. The system may include an encircling member and a fastening member that secures the encircling member in a loop around a portion of bone. In some embodiments, the fastening member may include any combination of the following: a cutting window, a guide aperture to guide a jaw of a crimping tool to a crimp region of the fastening member, multiple crimp regions, and/or apertures to receive adjustable prong members, among others.

22 Claims, 13 Drawing Sheets

(56) References Cited

U.S. PATENT DOCUMENTS

| | | |
|---|---|---|
| 3,641,629 A | 2/1972 | Beardsley |
| 3,754,303 A | 8/1973 | Pollock |
| 4,050,464 A | 9/1977 | Hall |
| 4,269,180 A | 5/1981 | Dall et al. |
| 4,473,925 A | 10/1984 | Jansen |
| 4,527,308 A | 7/1985 | Tritton et al. |
| 4,587,963 A | 5/1986 | Leibinger et al. |
| 4,643,178 A | 2/1987 | Nastari et al. |
| 4,688,560 A | 8/1987 | Schultz |
| 4,790,303 A | 12/1988 | Steffee |
| 4,896,668 A | 1/1990 | Popoff et al. |
| 5,051,543 A | 9/1991 | McGuire |
| 5,057,113 A | 10/1991 | Mingozzi |
| 5,116,340 A | 5/1992 | Songer et al. |
| 5,190,545 A | 3/1993 | Corsi et al. |
| 5,312,410 A | 5/1994 | Miller et al. |
| 5,318,566 A | 6/1994 | Miller |
| 5,356,412 A | 10/1994 | Golds et al. |
| 5,415,658 A | 5/1995 | Kilpela et al. |
| 5,476,465 A | 12/1995 | Preissman |
| 5,545,168 A | 8/1996 | Burke |
| 5,609,596 A | 3/1997 | Pepper |
| 5,649,927 A * | 7/1997 | Kilpela et al. .................. 606/74 |
| 5,653,711 A | 8/1997 | Hayano et al. |
| 5,665,088 A | 9/1997 | Gil et al. |
| 5,693,046 A | 12/1997 | Songer et al. |
| 5,702,399 A | 12/1997 | Kilpela et al. |
| 5,704,936 A | 1/1998 | Mazel |
| 5,720,747 A | 2/1998 | Burke |
| 5,741,259 A | 4/1998 | Chan |
| 5,741,260 A | 4/1998 | Songer et al. |
| 5,810,825 A | 9/1998 | Huebner |
| 5,902,305 A | 5/1999 | Beger et al. |
| 5,935,133 A | 8/1999 | Wagner et al. |
| 5,941,881 A | 8/1999 | Barnes |
| 5,993,449 A | 11/1999 | Schläpfer et al. |
| 5,993,452 A | 11/1999 | Vandewalle |
| 6,017,345 A | 1/2000 | Richelsoph |
| 6,017,347 A * | 1/2000 | Huebner et al. ................ 606/74 |
| 6,066,141 A | 5/2000 | Dall et al. |
| 6,120,505 A | 9/2000 | Huebner |
| 6,146,386 A | 11/2000 | Blackman et al. |
| 6,381,816 B1 * | 5/2002 | Lai et al. ..................... 24/712.9 |
| 6,616,667 B1 | 9/2003 | Steiger et al. |
| 7,229,444 B2 | 6/2007 | Boyd |
| 7,255,701 B2 | 8/2007 | Allen et al. |
| 8,486,114 B2 * | 7/2013 | Gillard et al. ................. 606/280 |
| 2001/0010110 A1 * | 8/2001 | Matsushima et al. ........... 24/130 |
| 2003/0079315 A1 * | 5/2003 | Malin ......................... 24/136 R |
| 2005/0124996 A1 | 6/2005 | Hearn |
| 2005/0137608 A1 | 6/2005 | Hearn et al. |
| 2005/0240198 A1 | 10/2005 | Albertson et al. |
| 2006/0058795 A1 | 3/2006 | Boyd |
| 2006/0276804 A1 | 12/2006 | Molz, IV et al. |
| 2007/0260248 A1 | 11/2007 | Tipirneni |
| 2008/0058815 A1 | 3/2008 | Young |
| 2010/0094294 A1 | 4/2010 | Gillard et al. |
| 2010/0133491 A1 * | 6/2010 | Lipke ........................... 254/389 |
| 2010/0319605 A1 * | 12/2010 | Petrenko ...................... 116/173 |
| 2013/0310879 A1 | 11/2013 | Gillard et al. |

FOREIGN PATENT DOCUMENTS

| | | |
|---|---|---|
| GB | 1205346 A | 9/1970 |
| GB | 2321672 B | 7/2001 |
| GB | 2476630 B | 1/2013 |
| JP | 59-39870 U | 3/1984 |
| JP | 1-124664 U | 8/1989 |
| JP | 2000-320730 A | 11/2000 |
| WO | 2010042946 A1 | 4/2010 |

OTHER PUBLICATIONS

Stryker Orthopaedics, Hip Systems—Dall-Miles Recon & Trauma Cable System product overview internet pages <http://www.stryker.com/jointreplacements/sites/dallmiles/overview.php>, printed Nov. 26, 2006; 8 pages.

PRWeb, "Pioneer Surgical Technology, Inc. Announces First Clinical Use of Tritium Sternal Cable Plating System", PRWeb ebooks press release, Jan. 22, 2013; 2 pages.

Copenheaver, Blaine R., Authorized Officer, International Searching Authority, International Search Report, International Application No. PCT/US2013/038904; search completion date: Aug. 12, 2013; mailing date: Aug. 15, 2013; 2 pages.

Copenheaver, Blaine R., Authorized Officer, International Searching Authority, Written Opinion of the International Searching Authority, International Application No. PCT/US2013/038904; search completion date: Aug. 12, 2013; mailing date: Aug. 15, 2013; 15 pages.

Codman & Shurtleff, Inc., SofWire Cable System brochure, undated; 6 pages.

* cited by examiner

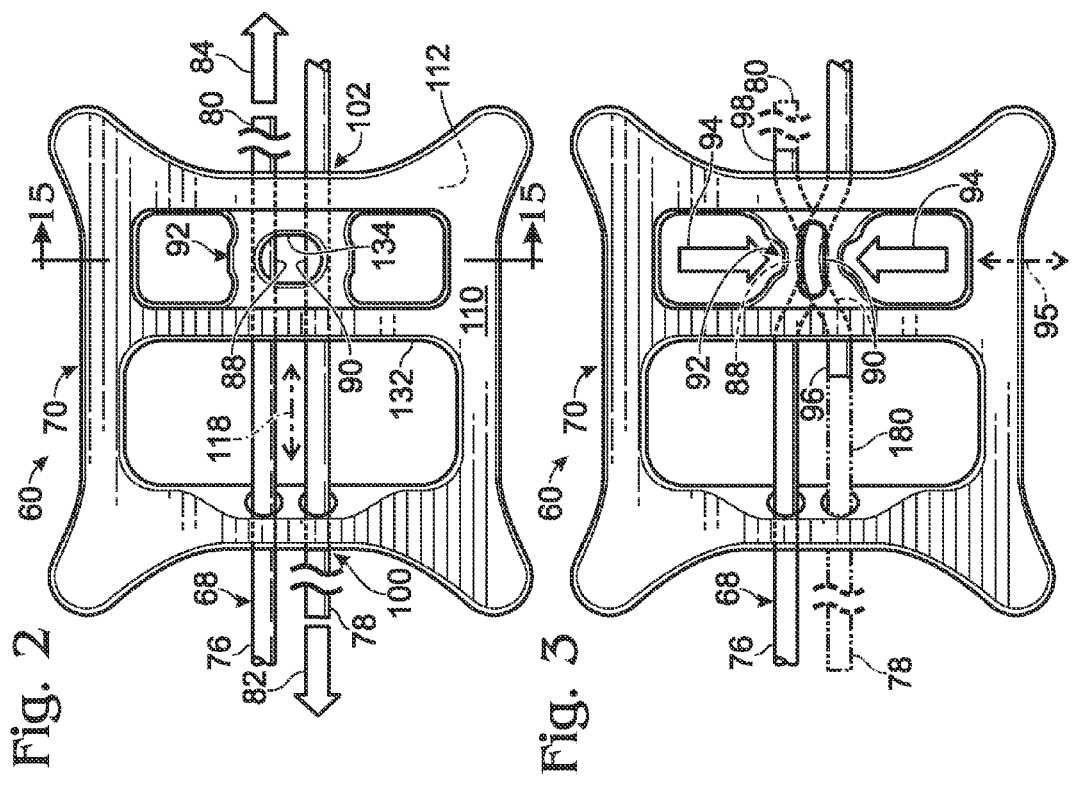
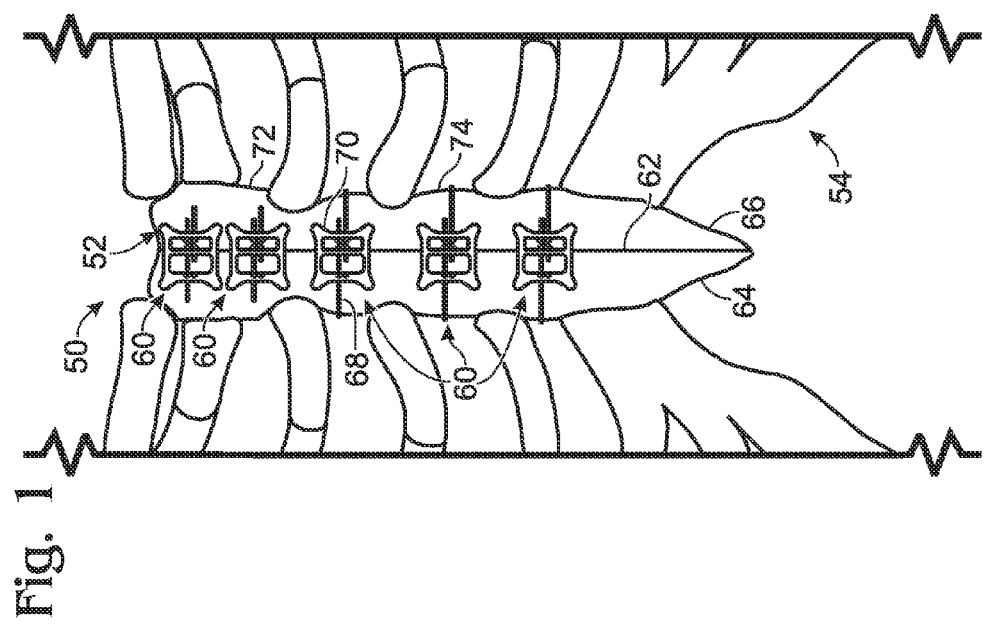
Fig. 2
Fig. 3
Fig. 1

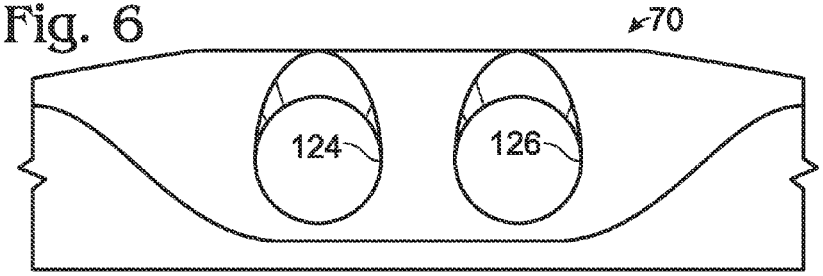
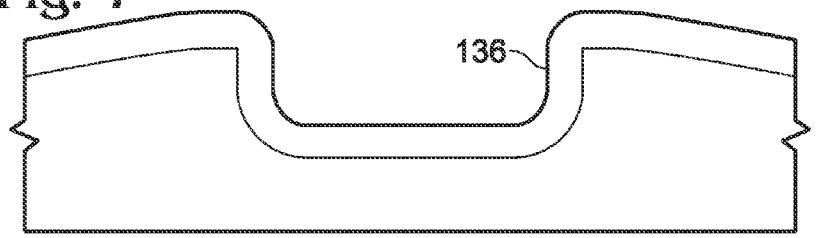
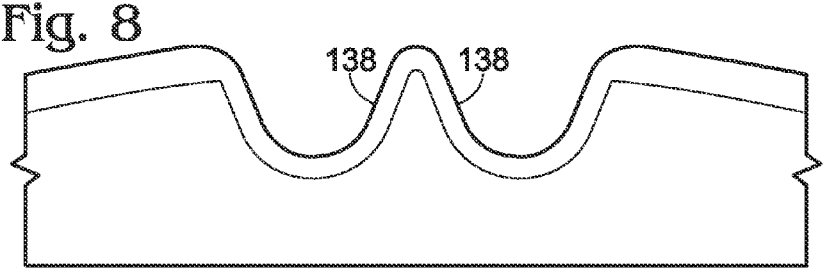
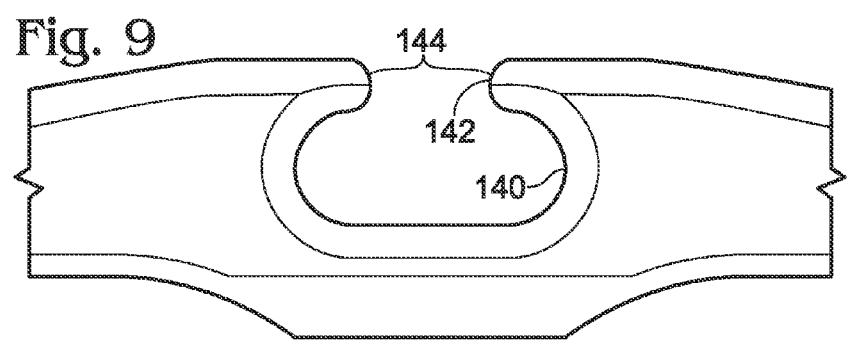
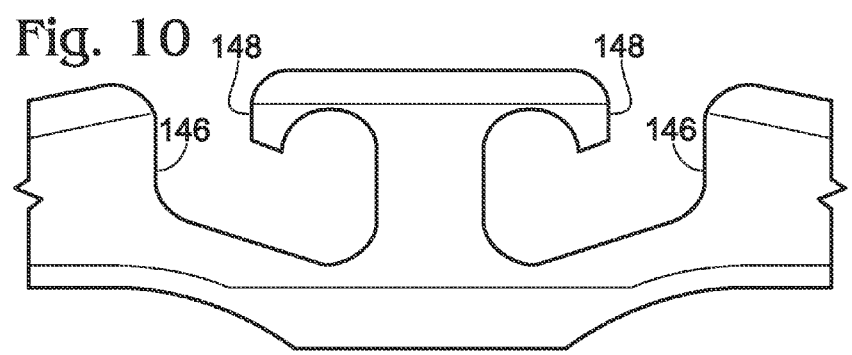

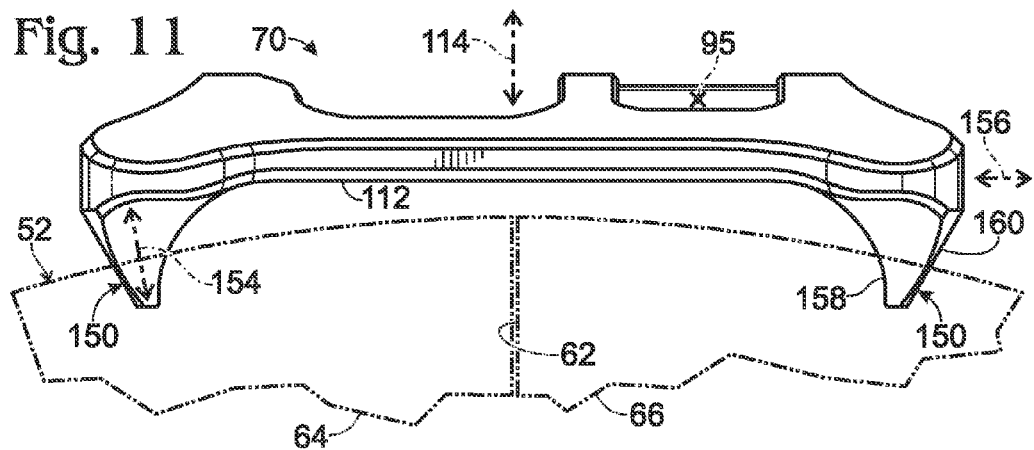
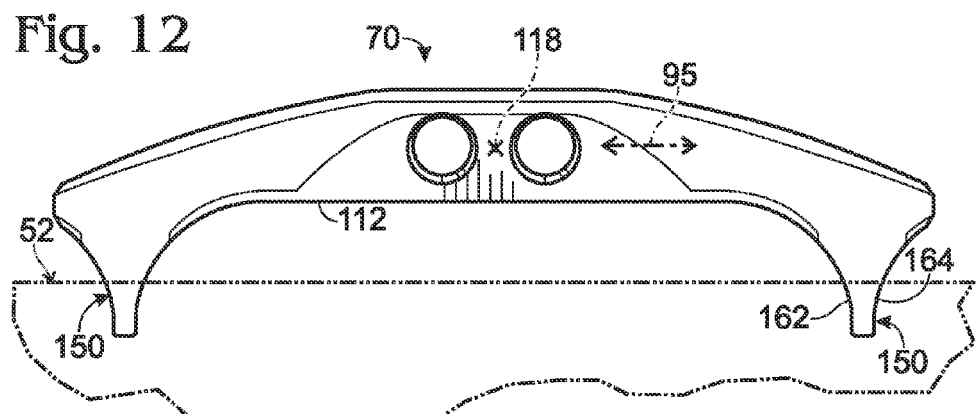
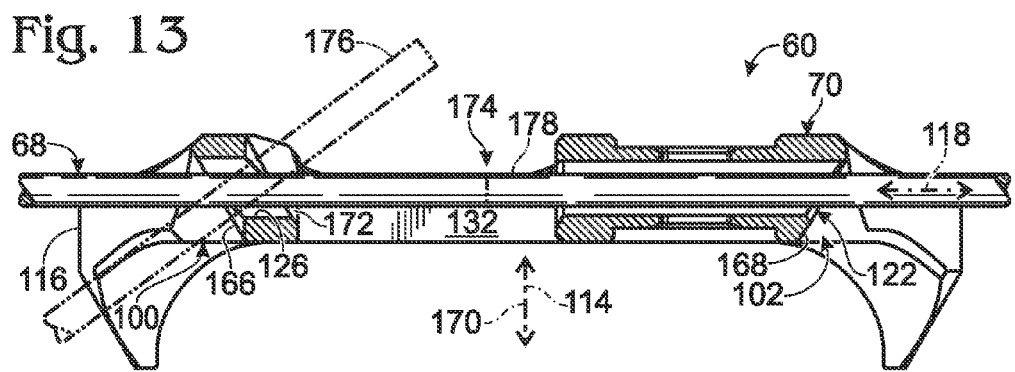

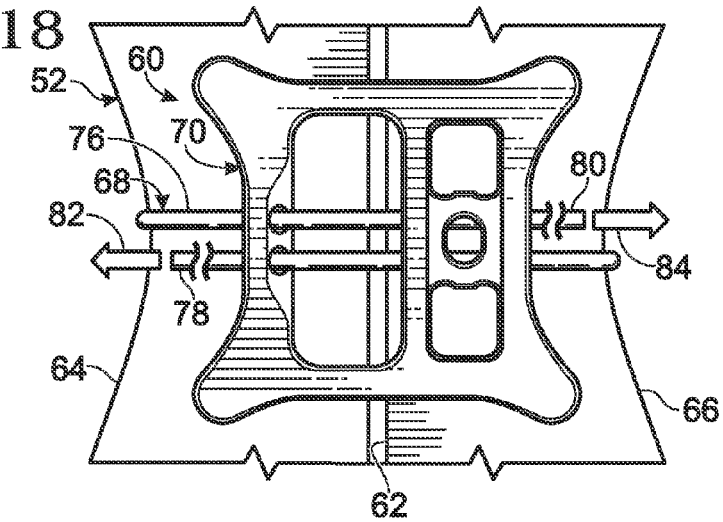
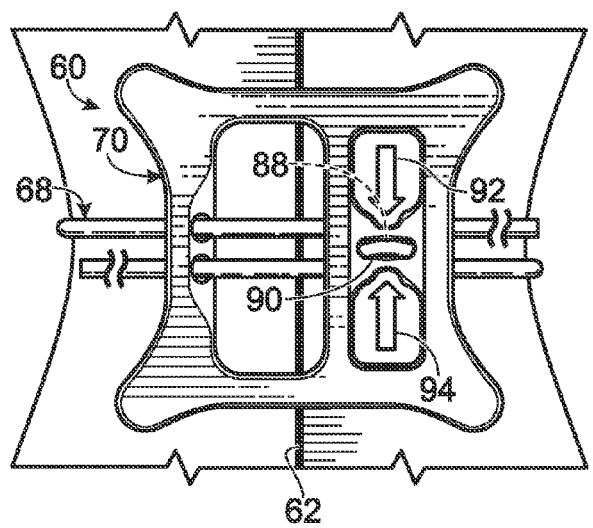
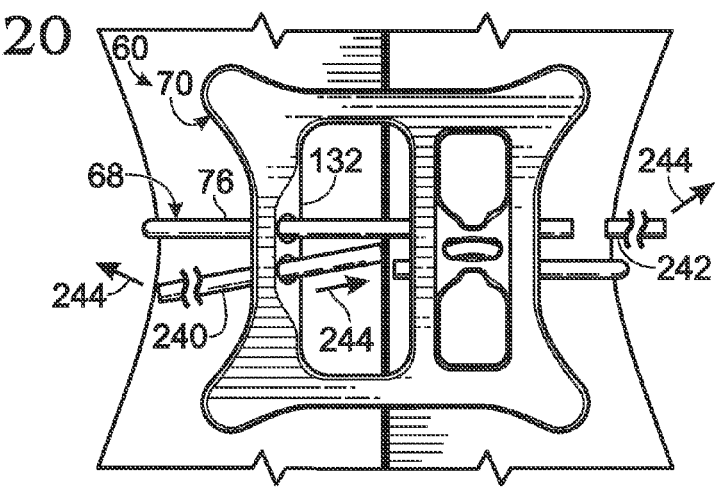

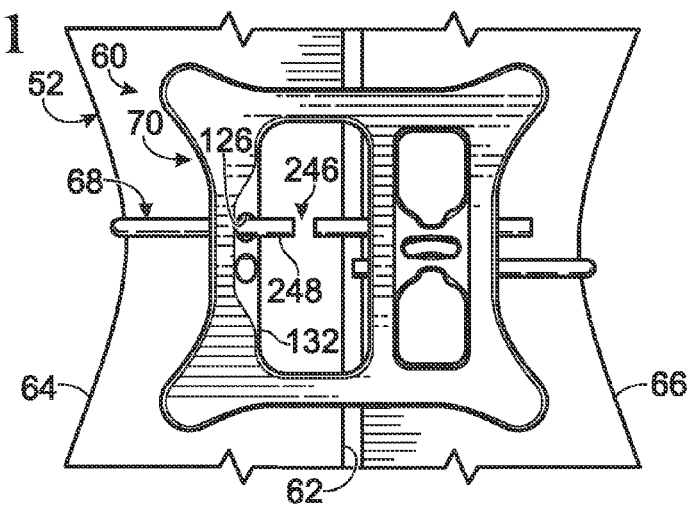
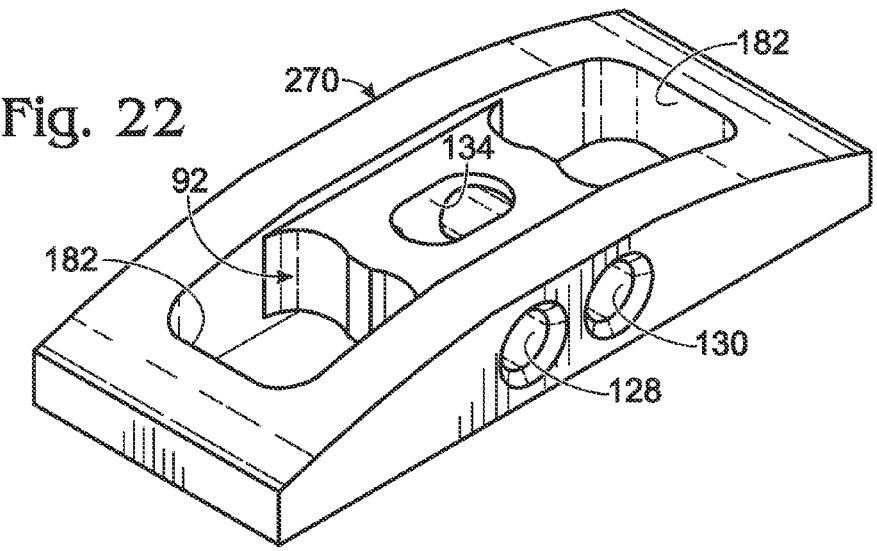
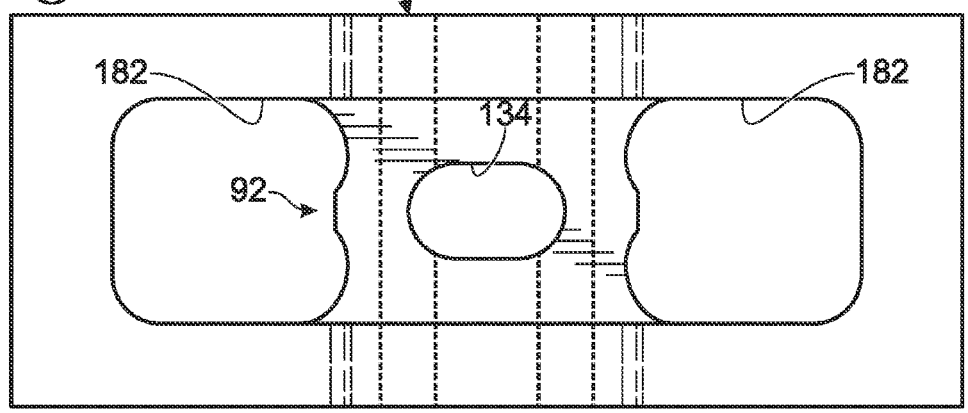

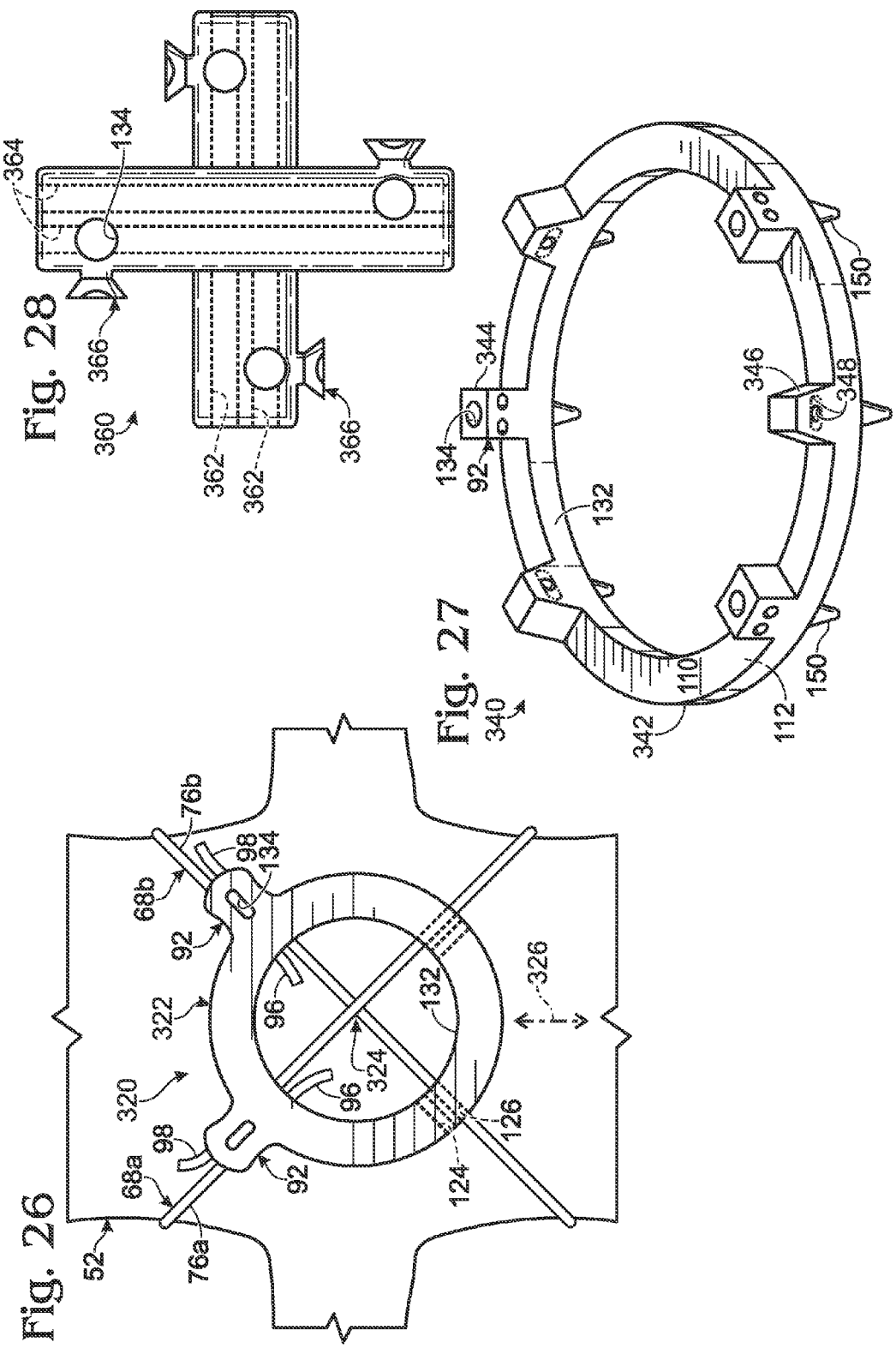

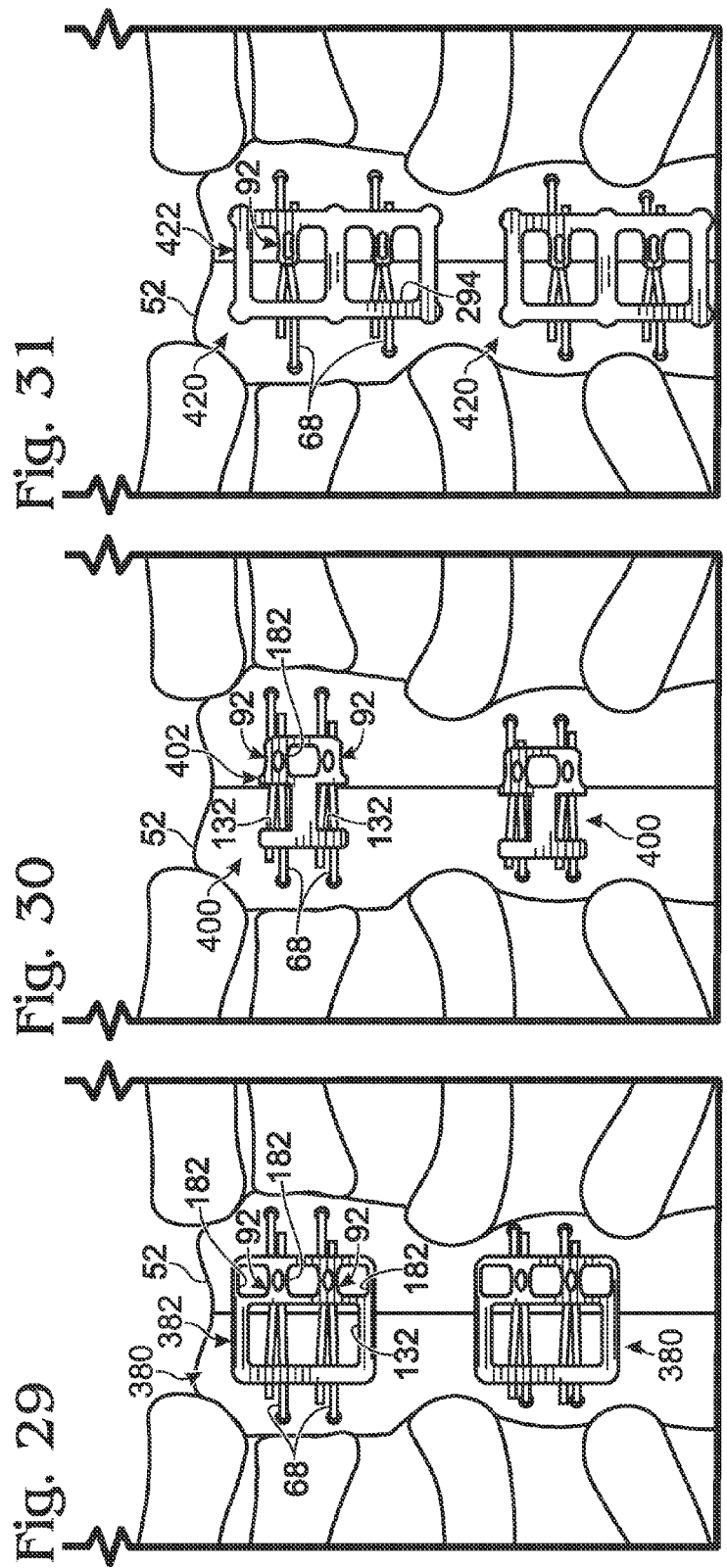

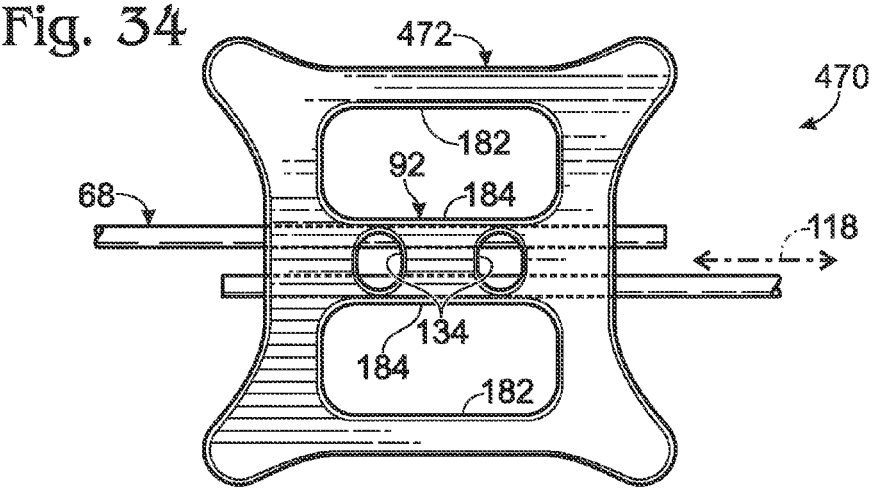
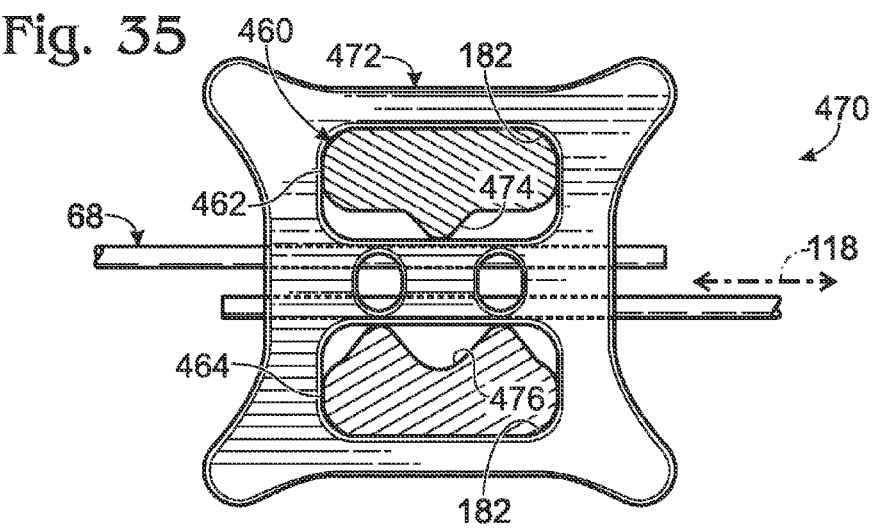
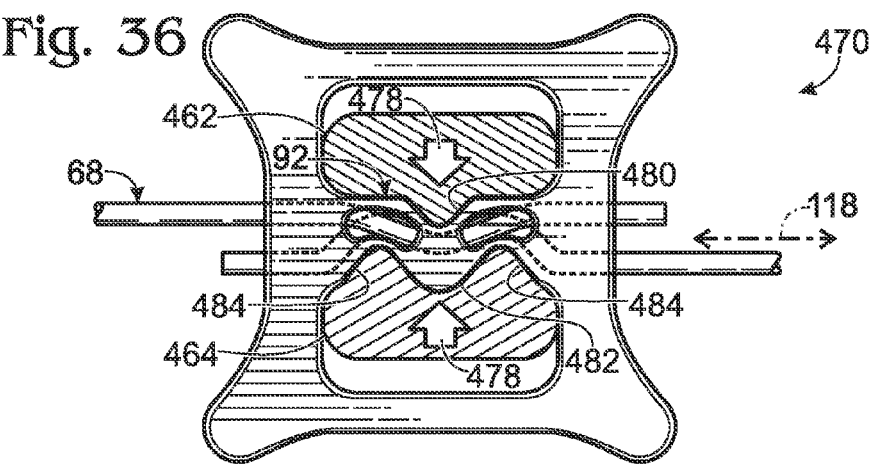

SYSTEM FOR BINDING BONE

CROSS-REFERENCES TO PRIORITY APPLICATIONS

This application is based upon and claims the benefit under 35 U.S.C. §119(e) of U.S. Provisional Patent Application Ser. No. 61/640,486, filed Apr. 30, 2012; and U.S. Provisional Patent Application Ser. No. 61/641,703, filed May 2, 2012. Each of these priority applications is incorporated herein by reference in its entirety for all purposes.

CROSS-REFERENCES TO OTHER MATERIAL

Each of the following patent documents is incorporated herein by reference in its entirety for all purposes: U.S. Pat. No. 6,017,347, issued Jan. 25, 2000; U.S. Patent Application Publication No. 2010/0094294 A1, published Apr. 15, 2010; and U.S. Patent Application Publication No. 2011/0112537 A1, published May 12, 2011.

INTRODUCTION

The rib cage, or thoracic cage, is composed of bone and cartilage that surround the chest cavity and organs therein, such as the heart and the lungs. In humans, the rib cage typically consists of 24 ribs, twelve thoracic vertebrae, the sternum (or breastbone), and the costal cartilages. The ribs articulate with the thoracic vertebrae posteriorly and, with the exception of the bottom two pairs of ribs (the floating ribs), are connected to the sternum anteriorly via the costal cartilages.

Major surgery inside the chest cavity, such as open heart surgery, requires that the rib cage be opened. A common procedure for opening the rib cage involves cutting the sternum. A surgeon may, for example, section the sternum with a J-cut, a T-cut, a longitudinal cut, or a transverse cut, among others. After surgery in the chest cavity has been completed, the sternum may be closed by approximating the sternal fragments and securing them to one another.

The surgeon may secure the sternum using a cerclage or binding procedure in which wires (or cables) bind the sternum at positions along the sternum. Each wire may be secured in a looped configuration using a fastening member. The fastening member may function to distribute the load exerted on the bone. As a result, the fastening member may reduce damage to bone by limiting the tendency of the wire to cut into and/or through bone. Also or alternatively, the fastening member may reduce breakage of the wire relative to securing the wire without a fastening member by twisting ends of the wire about one another, which weakens the wire.

An exemplary fastening member is disclosed in U.S. Patent Application Publication No. 2010/0094294 A1, and is structured as a plate for receiving the wire. The wire may be disposed in channels of the plate to form a loop, and the wire properly positioned and tensioned. Then, the plate may be crimped, to fasten both ends of the loop to the plate, thereby maintaining the wire in an encircling configuration around bone.

Despite various advantages offered by the plate described above, further improvements are still needed, such as to provide easier removal, more reliable attachment to a wire, better adjustability, more installation options, or the like.

SUMMARY

The present disclosure provides a system, including methods, apparatus, and kits for binding bone. The system may include an encircling member and a fastening member that secures the encircling member in a loop around a portion of bone. In some embodiments, the fastening member may include any combination of the following: a cutting window, a guide aperture to guide a jaw of a crimping tool to a crimp region of the fastening member, multiple crimp regions, and/or apertures to receive adjustable prong members, among others.

BRIEF DESCRIPTION OF THE DRAWINGS

FIG. 1 is an anterior view of a rib cage including a surgically-bisected sternum bound with multiple copies of an exemplary binding device of a cerclage system after open chest surgery, in accordance with aspects of the present disclosure.

FIG. 2 is a fragmentary plan view of a binding device of the system of FIG. 1, including an encircling member spanning a fastening member twice to form a loop, taken before the fastening member is crimped, in accordance with aspects of the present disclosure.

FIG. 3 is view of the binding device of FIG. 2 taken after the fastening member is crimped, in accordance with aspects of the present disclosure.

FIG. 6 is a fragmentary view of the fastening member of FIG. 2, taken generally along line 6-6 of FIG. 4 toward a lateral passage region from a cutting window defined by the fastening member.

FIG. 7 is a fragmentary view of another exemplary fastening member, taken generally as in FIG. 6 toward a lateral passage region formed as a single recess that is open on top, in accordance with aspects of the present disclosure.

FIG. 8 is a fragmentary view of still another exemplary fastening member, taken generally as in FIG. 6 toward a lateral passage region formed as a pair of recesses that are open on top, in accordance with aspects of the present disclosure.

FIG. 9 is a fragmentary view of yet another exemplary fastening member, taken generally as in FIG. 6 toward a lateral passage region formed as a single opening having a narrowed mouth, in accordance with aspects of the present disclosure.

FIG. 10 is a fragmentary view of still yet another exemplary fastening member, taken generally as in FIG. 6 toward a lateral passage region formed as a pair of U-shaped openings, in accordance with aspects of the present disclosure.

FIG. 11 is an elevational view of the fastening member of FIG. 2, taken generally along 11-11 of FIG. 4 with the fastening member positioned on a region of a bisected sternum, which is shown fragmentarily and schematically in phantom lines, in accordance with aspects of the present disclosure.

FIG. 12 is an elevational view of the fastening member of FIG. 2, taken generally along line 12-12 of FIG. 4 with the fastening member positioned on the sternum of FIG. 11, in accordance with aspects of the present disclosure.

FIG. 13 is a sectional view of the fastening member of FIG. 2, taken generally along line 13-13 of FIG. 5 in the presence of an encircling member extending through a passage of the fastening member and spanning a window defined by the fastening member, with a cut form of the encircling member shown in phantom outline, in accordance with aspects of the present disclosure.

FIG. 18 is a fragmentary view of the binding device of FIG. 2 encircling a sternum, taken toward an anterior side of the sternum before the fastening member has been crimped and while the encircling member is being tensioned, in accordance with aspects of the present disclosure.

FIG. 19 is another fragmentary view of the binding device and sternum of FIG. 18, taken after the fastening member has been crimped to attach the ends of an encircling-member loop to the fastening member, in accordance with aspects of the present disclosure.

FIG. 20 is still another fragmentary view of the binding device and sternum of FIG. 18, taken after opposing end regions of the encircling member outside the loop have been severed, in accordance with aspects of the present disclosure.

FIG. 21 is still yet another fragmentary view of the binding device and sternum of FIG. 18, taken after the encircling-member loop has been cut within the window of the fastening member to allow removal of the binding device from the sternum, in accordance with aspects of the present disclosure.

FIG. 22 an isometric view of another exemplary fastening member for the cerclage system of FIG. 1, in accordance with aspects of the present disclosure.

FIG. 23 is a plan view of the fastening member of FIG. 22.

FIG. 26 is a plan view of an exemplary binding device stabilizing a sternum and including a pair of encircling members secured around the sternum in a crossed configuration with the same fastening member, in accordance with aspects of the present disclosure.

FIG. 27 is an isometric view of an exemplary fastening member configured to secure three copies of an encircling member, in accordance with aspects of the present disclosure.

FIG. 28 is a plan view of an exemplary fastening member configured to secure a pair of encircling members extending around bone in a crossed configuration, in accordance with aspects of the present disclosure.

FIG. 29 is a plan view of a pair of copies of an exemplary binding device stabilizing a cut sternum and each including a pair of encircling members secured around a portion of the sternum in a parallel configuration with the same fastening member, in accordance with aspects of the present disclosure.

FIG. 30 is a plan view of a pair of copies of another exemplary binding device stabilizing a cut sternum and each including a pair of encircling members secured around a portion of the sternum in a parallel configuration with the same fastening member, in accordance with aspects of the present disclosure.

FIG. 31 is a plan view of a pair of copies of still another exemplary binding device stabilizing a cut sternum and each including a pair of encircling members secured around a portion of the sternum in a parallel configuration with the same fastening member, in accordance with aspects of the present disclosure.

FIG. 34 is a fragmentary plan view of an exemplary binding device in an encircling configuration before the binding device is crimped, in accordance with aspects of the present disclosure.

FIG. 35 is a fragmentary plan view of the binding device of FIG. 34, taken after jaws of an exemplary crimping tool have been mated with a fastening member of the binding device, with the jaws shown in cross-section, in accordance with aspects of the present disclosure.

FIG. 36 is a fragmentary plan view of the binding device and a sectional view of the jaws of FIG. 35, taken after the jaws of the crimping tool have crimped a crimp region of the fastening member, in accordance with aspects of the present disclosure.

DETAILED DESCRIPTION

Figure 4:
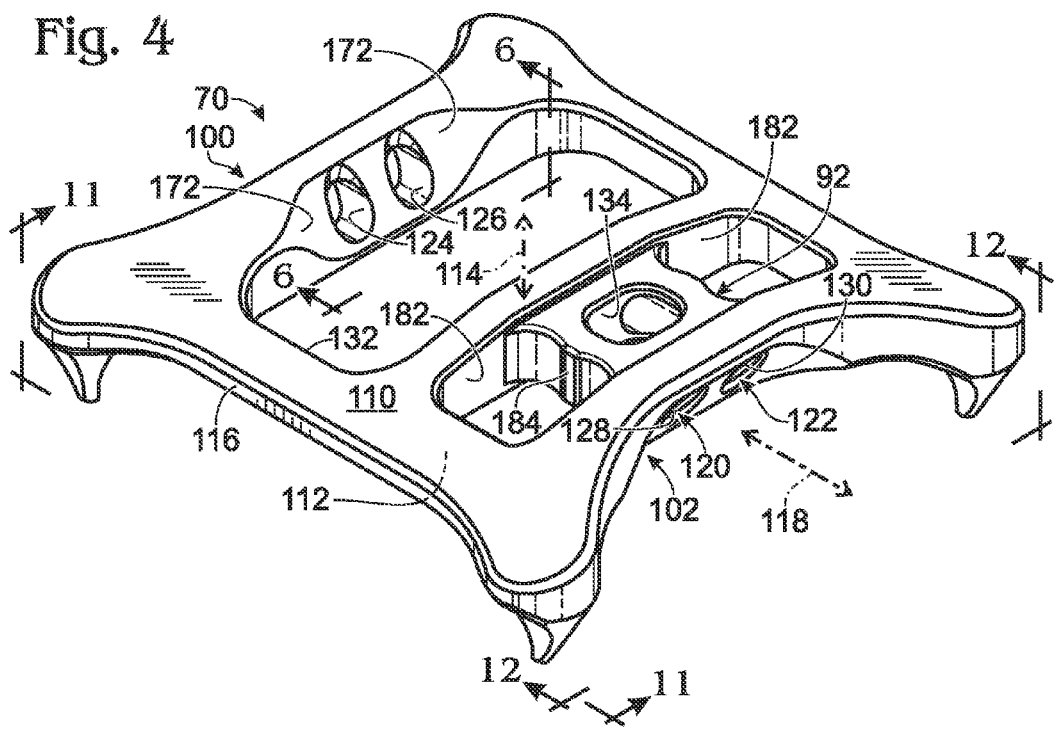
FIG. 4 is an isometric view of the fastening member of the binding device of FIG. 2, taken in isolation from the encircling member.

The present disclosure provides a system, including methods, apparatus, and kits for binding bone. The system may include an encircling member and a fastening member that secures the encircling member in a loop around a portion of bone. In some embodiments, the fastening member may include any combination of the following: a cutting window, a guide aperture to guide a jaw of a crimping tool to a crimp region of the fastening member, multiple crimp regions, and/or apertures to receive adjustable prong members, among others.

These and other aspects of the present disclosure are described in the following sections: (I) exemplary cerclage system for bone, (II) exemplary crimping tool, (III) installation, (IV) system combinations; and (V) examples.

I. Exemplary Cerclage System For Bone

This section describes selected aspects of an exemplary cerclage system 50 (interchangeably termed a bone binding system); see FIGS. 1-13.

FIG. 1 shows an anterior view of a surgically-sectioned sternum 52 of a rib cage 54 closed with cerclage system 50, in this case, with multiple copies of an exemplary binding device 60 of system 50. Here, the sternum has been cut along its length to form a longitudinal discontinuity 62 that divides the sternum into left and right sternal halves or fragments 64, 66. Each binding device 60 may span discontinuity 62 twice (i.e., exactly or at least twice), and may encircle a portion of sternum 52, to stabilize the sternum by holding fragments of the sternum together and to keep the rib cage closed (e.g., after open chest surgery). In other examples, the cerclage system may stabilize a sternum cut differently (e.g., transversely, in a J-shape, in a T-shape, or a combination thereof, among others), a fractured sternum, or may be installed on the sternum or any other suitable bone, with or without a discontinuity present in the bone.

Each binding device 60 may include at least one encircling member 68 and a fastening member 70 that secures at least two longitudinally-spaced regions of the encircling member to the fastening member. Other exemplary system components are described elsewhere in the present disclosure, such as in Sections II-V.

Each encircling member may be any elongate member that is of sufficient length and flexibility to be arranged in a loop, for example, a loop that encircles a portion of bone. The encircling member may be strong enough to be tensioned to compress bone. The encircling member may have a smooth surface to facilitate sliding the encircling member through openings of the fastening member, and/or may include surface structure, such as recesses and/or protrusions, to resist sliding after the encircling member has been attached to the fastening member. The encircling member may have any suitable cross-sectional shape including circular, oval, polygonal (e.g., rectangular), or any combination thereof, among others. Exemplary encircling members may include a wire, a cable, a strap, a suture, or the like.

In exemplary embodiments, the encircling member includes a wire or a cable, which may be formed of metal. The terms "wire" and "cable" in surgical applications generally denote respective single-stranded and multi-stranded structures. Wires and cables thus may have distinct uses and properties (e.g., distinct flexibilities and tendencies to kink and fray). However, throughout the present disclosure, a wire or a cable may be utilized as an encircling member in a cerclage apparatus or method.

Each fastening member interchangeably may be termed an anchor member or a plate member. The fastening member may be less flexible than the encircling member and may provide a stable platform from which the encircling member can extend around a portion of bone. The fastening member may be disposed at least mostly outside bone, adjacent any suitable surface region of bone. For example, here, fastening member 70 is disposed on the anterior surface region of sternum 52.

The encircling member and the fastening member each may have any suitable composition. Each may be formed of any suitable biocompatible material(s) and/or bioresorbable (bioabsorbable) material(s). Illustrative biocompatible materials that may be suitable for an encircling member or a fastening member include (1) metal (for example, titanium or titanium alloy, cobalt-chrome alloy, stainless steel, etc.); (2) plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals e.g., hydroxyapatite, carbonated apatite, etc.)); or (5) any combination thereof.

The encircling member and the fastening member may be formed of the same or different materials. For example, both may be formed of metal, both may be formed of plastic, both may be bioresorbable, the encircling member may be formed of metal and the fastening member of plastic (which may be bioresorbable) (or vice versa), or the like.

Cerclage system 50 may utilize one or more binding devices 60. For example, in the present illustration, manubrium 72 of the sternum is secured with a superior pair of discrete binding devices 60, which each extend through the sternum, rather than completely around the circumference of the sternum. Accordingly, each of these more superiorly-positioned binding devices encircles only an anterior portion of the sternum. In contrast, body 74 of the sternum is secured with a more inferiorly-positioned trio of binding devices 60, which each extend completely around the sternum at three distinct positions spaced from one another along sternum 52.

FIG. 2 shows one of binding devices 60 of FIG. 1 in an assembled configuration before the binding device is crimped. Encircling member 68 may extend from fastening member 70, around a portion of bone, and back to fastening member 70, to form a loop 76 and a pair of free ends 78, 80 extending from the loop and each having any suitable length. Free ends 78, 80 may be pulled in opposite directions, indicated by tension arrows 82, 84, to tighten loop 76 around bone.

FIGS. 2 and 3 respectively show binding device 60 before and after the binding device is crimped. Loop 76 has loop ends 88, 90 that are secured to fastening member 70 by at least one crimp region 92 (interchangeably termed a pinch region or deformable region) of the fastening member. Crimp region 92 may be deformed (e.g., pressed together), as indicated by compression arrows 94 in FIG. 3, to engage (e.g., grip) one or both loop ends 88, 90, which may also be crimped (interchangeably termed deformed) by deformation of the crimp region. Compression may be applied parallel to a compression axis 95 (which may be linear or curved). In some cases, a pair of crimp regions each may secure a distinct end of the loop. In the installation configuration shown in FIG. 3, each free end 78, 80 may or may not be truncated (indicated in phantom outline), after the binding device is crimped and at a position inside or outside fastening member 70. For example, here, both free ends have been truncated or severed to form stubs 96, 98 that extend from respective loop ends 90 and 88 to opposing longitudinal boundaries of the encircling member. Stubs 96 and 98 respectively terminate inside and outside the perimeter of the fastening member. In other embodiments, both stubs may terminate inside the perimeter or both may terminate outside the perimeter of the fastening member.

Loop ends 88, 90 may overlap each other in crimp region 92 (see FIG. 3). The ends may be placed through crimp region 92 on spaced paths (e.g., parallel paths) and then may be urged toward and/or into contact with one another by deforming the crimp region. In some cases, loop ends 88, 90 may be disposed laterally to each other before the crimp region is deformed (as in FIG. 2), and then above and below one another after the crimp region is deformed (as in FIG. 3).

Encircling member 68 may span fastening member 70 one or more times, before and/or after the crimp region is deformed. For example, in FIG. 2, encircling member 68 spans fastening member 70 twice by extending twice through the fastening member between spaced sites 100, 102 that are opposite one another across the fastening member.

Figure 5:
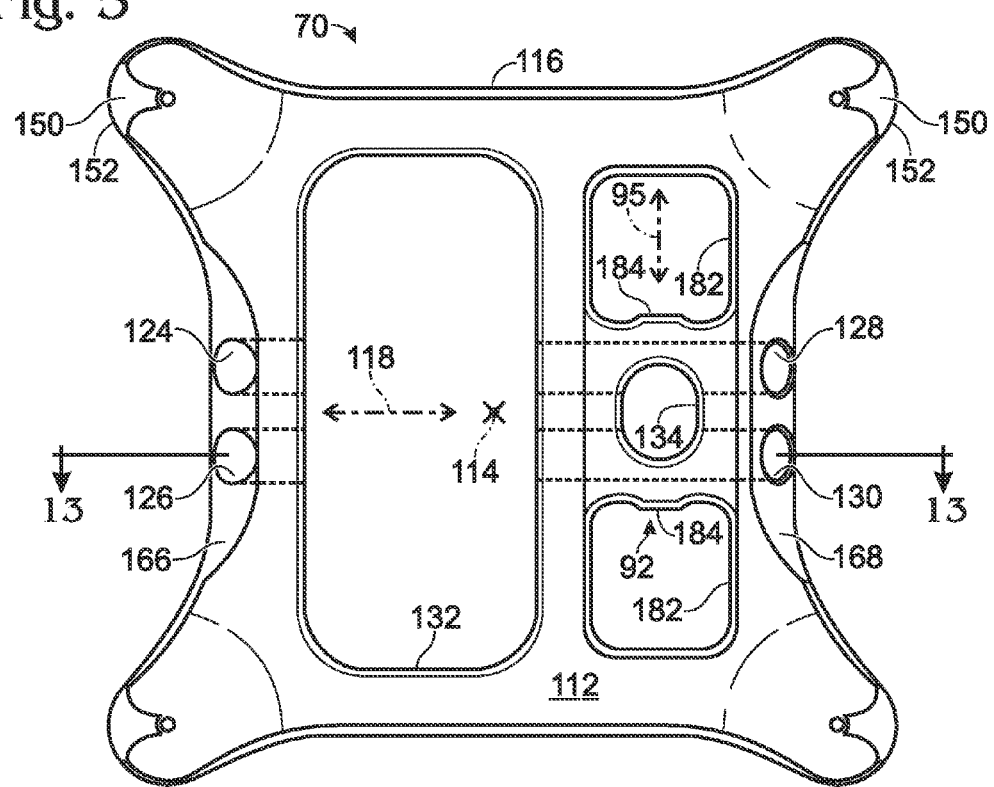
FIG. 5 is a bottom view of the fastening member of FIG. 2, taken in isolation from the encircling member.

FIGS. 2, 4, and 5 show further aspects of fastening member 70. The fastening member may include a top surface region 110 opposite a bottom surface region 112. The top surface region (interchangeably termed an outer surface region) may be configured to face away from the bone portion to which the binding device is attached. The bottom surface region (interchangeably termed an inner or bone-facing surface region) may be configured to face toward the bone portion to which the binding device is attached. The fastening member defines a height axis (interchangeably termed a vertical axis), such as central height axis 114, arranged orthogonally to surface regions 110 and 112 see FIGS. 4 and 5).

In some embodiments, the fastening member may have a top surface region and a bottom surface region that are interchangeable. For example, the fastening member may have reflectional symmetry with respect to a horizontal plane, allowing the fastening member to be installed with either surface region facing bone.

A perimeter side wall region 116 (interchangeably termed a lateral side wall region) is disposed between top surface region 110 and bottom surface region 112 and defines a perimeter of the fastening member (see FIGS. 4 and 5). The lateral side wall region may be centered around central height axis 114. The side wall region may or may not form a distinct edge with top surface region 110 and/or bottom surface region 112 at each position around the fastening member where the lateral side wall region meets either surface region. Accordingly, the lateral side wall region may transition smoothly to either or both surface regions 110 and 112 at none, any, or all positions around the fastening member.

A fastening member may define at least one path or passage, or two or more paths or passages, through which the encircling member may extend one or more times through the fastening member and/or the crimp region thereof. The encircling member may extend parallel to a spanning axis 118 defined by the fastening member (see FIGS. 4 and 5). For example, fastening member 70 defines paths/passages 120 and 122. Each passage may extend between lateral side wall sites 100, 102 on a path that is intermediate top surface region 110 and bottom surface region 112, such as at an average elevation between the average elevations of surface regions 110 and 112. Accordingly, the encircling member may be elevated from bottom surface region 112 between the ends of each passage. Each path may be substantially parallel to one or both surface regions 110 and 112 and may be substantially linear.

Passages 120 and 122 may be formed by a plurality of openings defined by fastening member 70 (see FIGS. 4 and 5). Each opening may form at least part of only one of the passages or of two or more passages. For example, fastening member 70 may define a pair of channels 124 and 126 that extend separately into fastening member 70 from lateral side wall site 100 and form respective ends of passages 120 and 122. Also, fastening member 70 may define another pair of channels 128, 130 that extend separately into fastening member 70 from opposite site 102 and form respective opposite ends of passages 120 and 122. Each of channels 124, 126, 128, and 130 may be circumferentially bounded. If circumferentially bounded, the channel has a completely bounded or closed perimeter, as shown here. Alternatively, any of the channels may lack a closed perimeter (e.g., may be open above or below the channel). Each passage also may be formed in part by, may intersect, and/or may extend through at least one window 132 (see FIGS. 2, 4, and 5) and/or at least one collapsible aperture 134 (compare FIGS. 2 and 3). Window 132 and collapsible aperture 134 each may be through-openings that extend from top surface region 110 to bottom surface region 112.

The window may formed by a large opening (e.g., the largest opening) defined by the fastening member. The window may have a characteristic dimension, measured on a line parallel to the top/bottom surface region of the fastening member, that is greater than one-fourth or one-half of a corresponding dimension of the fastening member measured at the perimeter of the fastening member along the same line. Alternatively or in addition, the window may have an area that is more than one-tenth, one-fourth, or one-half of the area enclosed by the perimeter of the fastening member.

FIG. 6 shows channels 124 and 126 viewed from window 132. The channels each may circumferentially bounded between opposing ends and spaced laterally from each other.

FIGS. 7-10 show other embodiments of openings that may replace channels 124 and 126 (and/or channels 128 and 130 on only one side or opposite sides of collapsible aperture 134). FIG. 7 shows a fastening member having a single recess or concavity 136 that is open on top and has vertical walls. FIG. 8 shows a fastening member having a pair of recesses or concavities 138 that are open on top. FIG. 9 shows a fastening member having a single opening 140 that tapers upward to form a narrowed mouth or gap 142 disposed above and communicating with a body of the opening. The opening may be sized to receive the encircling member twice, with lips 144 of mouth 142 configured to retain the encircling member in the opening. In some embodiments, opening 140 may be closed on top to form a bounded perimeter. FIG. 10 shows a fastening member having a pair of U-shaped openings 146. A hook region or lip 148 of each opening can retain the encircling member in the opening.

FIGS. 5, 11, and 12 show cleats, such as prongs 150, that may project from bottom surface region 112 of fastening member 70. A cleat may be any downwardly projecting member to position and/or resist slippage of the fastening member on bone. A prong may be any cleat that tapers downwardly in a direction away from the body of the fastening member. The fastening member may have any suitable number of cleats, such as none, only one, at least a pair, or three or more. Each cleat may be formed integrally (e.g., as part of a one-piece fastening member), as in fastening member 70, or may be formed as a separate piece (e.g., see Example 2). A majority of the cleat, by length measured orthogonal to bottom surface region 112, may or may not be disposed in bone and/or soft tissue over bone after the fastening member is installed. The cleat may or may not have rotational symmetry and/or reflectional symmetry. The cleat may have a length by which the cleat projects from bottom surface region 112, and a (maximum) width/diameter measured orthogonal to the length. The length may be greater than the width, about the same as the width, or less than the width.

FIG. 5 shows prongs 150 disposed under tabs 152 (interchangeably termed lateral protrusions) of fastening member 70. Each tab 152 may be formed as a rounded and/or elongated corner of fastening member 70, or may project from the body of the fastening member at any other suitable position, such as intermediate a pair of corners formed by the fastening member, among others.

FIGS. 11 and 12 show a pair of side views of fastening member 70, taken orthogonally to each other, with sternum 52 illustrated schematically in phantom lines. In each case, bottom surface region 112 of fastening member 70 is elevated from the sternum by prongs 150. Accordingly, the prongs may allow the fastening member to be used on a nonplanar surface, such as a convex bone surface as in FIG. 11. Elevation of the fastening member above bone may offer substantial advantages to the surgeon, such as better access to encircling member 68 and/or fastening member 70 with tools (e.g., a tensioning tool, a crimping tool, a cutting tool, etc.), among others.

FIG. 11 shows prongs 150 having an asymmetrical profile when viewed parallel to compression axis 95. Each prong 150 may define a prong axis 154 oriented obliquely to a plane 156 defined by bottom surface region 112. An inner side 158 of the prong may be concave in profile and an outer side 160 of the prong may be less concave, linear, or convex in profile, among others. The asymmetrical profile depicted here may resist distraction of sternal fragments, and may facilitate compression of sternum 52 as encircling member 68 is tensioned.

FIG. 12 shows prongs 150 having a symmetrical profile when viewed parallel to spanning axis 118. The profile of each prong may be concave, linear, or convex on both inner and outer sides 162, 164.

FIG. 13 shows a sectional view of fastening member 70 taken through passage 122 with encircling member 68 extending through the passage. Fastening member 70 may have an opposing pair of chamfers 166, 168 formed at opposite ends of each passage 120 and 122 (also see FIGS. 4 and 5, among others). Each of chamfers 166 and 168 may be defined by a portion of lateral side wall region 116 that is undercut (or shaped as if undercut) to form an overhang. Each chamfer may slope inwardly, namely, toward a central plane 170 orthogonal to spanning axis 118, as the chamfer extends away from top surface region 110 and toward bottom surface region 112. Stated another way, the chamfers may slope convergently as each chamfer extends toward bottom surface region 112.

Undercut chamfers 166 and 168 may provide substantial advantages over the absence of chamfers, and particularly over chamfers that slope in the opposite direction ("overcut chamfers"). During installation of a binding device, application of tension to the encircling member, with the encircling member in a looped configuration, can apply a torque to the fastening member that causes the fastening member to flip over to an upside-down orientation on bone. A surgeon can prevent this undesired reorientation of the fastening member by clamping the fastening member to bone before the encircling member is tensioned. Undercut chamfers may stabilize the correct, right-side-up orientation of the fastening member, such that tensioning the encircling member can be performed without clamping the fastening member to bone, thereby saving time and effort.

Fastening member 70 also may have a chamfer 172 formed by a side wall region of window 132, at the opposite end of each channel 124, 126 (see FIGS. 4 and 13). Chamfer 172 may be an overcut chamfer that slopes at least in the same general direction as undercut chamfer 166 (e.g., parallel to the undercut chamfer), namely, toward central plane 170. Chamfers 166 and 172 may cooperate to offer greater pivotal mobility to encircling member 68, or a longitudinal piece cut therefrom. For example, encircling member may be cut in window 132, indicated by an arrow at 174, to form new ends 176, 178. Chamfers 166, 172 allow end 176 to be pivoted upward, to permit the end to be manipulated further, such as removed from channel 126. End 176 may be created by cutting at a site within the secured loop of the encircling member (e.g., to open the loop and remove the binding device) or outside the loop (e.g., to create piece 180 and stub 96 by cutting free end 78; see FIG. 3), among others.

FIGS. 4 and 5 show further aspects of crimp region 92. Fastening member 70 may define at least one alignment aperture (e.g., a pair of alignment apertures 182) that allows the jaws of a crimping tool to be guided to and operatively positioned against opposite contact sites 184 of crimp region 92. (Each alignment aperture interchangeably may be termed a guide aperture.) Contact sites 184 may be arranged at respective spaced positions along compression axis 95 and may face away from each other. Each contact site may be provided, at least in part, by a projecting portion (e.g., a button) of a wall region of each alignment aperture 182, as shown here, may be flush with flanking wall regions of aperture 182, or may be recessed (e.g., see Example 5). In any event, the contact sites may be moved closer to each other and deformed when the contact sites are squeezed with the crimping tool and crimp region 92 is deformed (e.g., compare FIGS. 2 and 3). Deforming the crimp region may secure both ends of an encircling-member loop to the fastening member at the same time. Alternatively, the ends of the loop may be secured/crimped serially by crimping a pair of crimp regions of the fastening member at different times (e.g., see Example 3 and U.S. Patent Application Publication No. 2010/0094294 A1, published Apr. 15, 2010, which is incorporated herein by reference).

Further aspects of binding devices that may be suitable are described elsewhere in the present disclosure, such as in Section V, and in the references identified above under Cross-References, which are incorporated herein by reference, particularly U.S. Provisional Patent Application Ser. No. 61/640, 486, filed Apr. 30, 2012; U.S. Provisional Patent Application Ser. No. 61/641,703, filed May 2, 2012; U.S. Patent Application Publication No. 2010/0094294 A1, published Apr. 15, 2010; and U.S. Pat. No. 6,017,347, issued Jan. 25, 2000.

II. Exemplary Crimping Tool

This section describes an exemplary crimping tool 200 that may be utilized to crimp any of the fastening members disclosed herein, to secure an encircling member to the fastening member and bone; see FIGS. 14-17.

Figure 14:
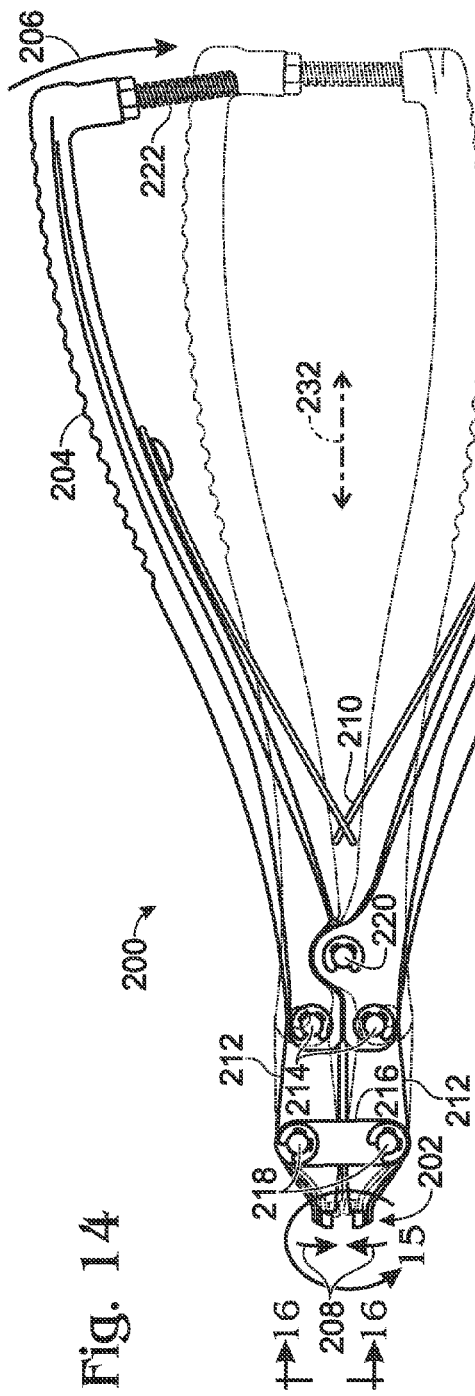
FIG. 14 is a side view of an exemplary crimping tool that may be used to crimp the fastening member of FIG. 2, to secure both ends of a loop formed by an encircling member that spans the fastening member, in accordance with aspects of the present disclosure.

FIG. 14 shows crimping tool 200 in a more open configuration (solid lines) (before crimping) and a less open configuration (phantom lines) (after crimping). The crimping tool has a pair of jaws 202 operatively connected to a pair of actuating member or levers 204, which are configured to be engaged and manipulated manually (e.g., with only one hand). Squeezing the actuating levers toward each other, indicated by arrows at 206, also urges jaws 202 toward each other, indicated by arrows at 208. The separation of the jaws from each other is decreased, as is the size of a gap defined between the jaws. A biasing member 210 (e.g., a leaf spring) may return levers 204 to the more open configuration when the pressure on the levers is sufficiently reduced or discontinued.

Jaws 202 may be provided by respective clamping members 212 that are pivotally connected to levers 204 at pivot joints 214 (e.g., hinge joints). The clamping members may be connected to each other by a connecting member 216, which may be rigid, to form a respective pivot joint 218 (e.g., a hinge joint) with each clamping member 212.

Levers 204 may be pivotally connected to each other at a pivot joint 220 (e.g., a hinge joint). Squeezing the levers causes the levers to pivot relative to one another at pivot joint 220, which moves pivot joints 214 away from one another. As the pivot joints move, clamping members 212 pivot in opposite pivotal directions at pivot joints 218, to bring the jaws closer together. A travel stop 222 at the proximal end of one or both of levers 204 may determine the permitted range of motion of the levers toward each other, which in turn may determine how closely the jaws can approach each other (and how much the crimp region of the fastening member can be deformed). The travel stop may be adjustable to change the minimum separation of the jaws, to increase or decrease the extent to which the crimp region is crimped/deformed by the tool.

Figure 15:
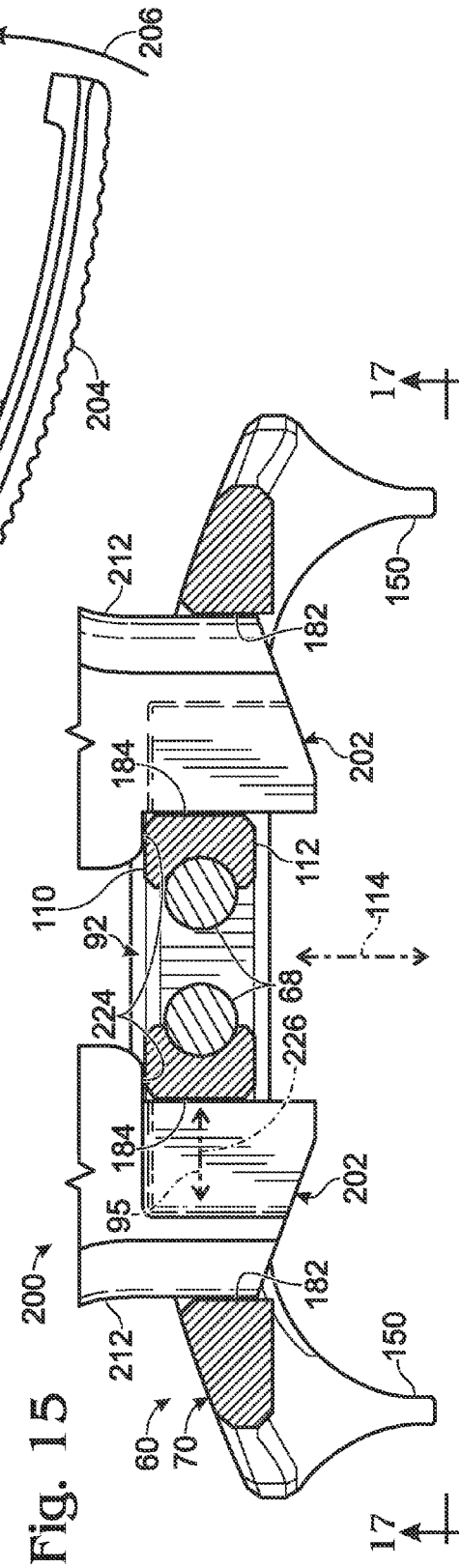
FIG. 15 is a magnified view of the crimping tool of FIG. 14, taken generally around the region indicated at "15" in FIG. 14, with the jaws of the crimping tool mated with the binding device of FIG. 2 such that the jaws are aligned with a crimp region of the fastening member, and with the binding device taken in cross section generally along line 15-15 of FIG. 2, in accordance with aspects of the present disclosure.

FIG. 15 shows a fragmentary view of the distal end of crimping tool 200, with jaws 202 mated with respective guide apertures 182 of fastening member 70. Each jaw 202 may be disposed adjacent and distal to a shoulder or stop region 224 of the corresponding clamping member 212. Each shoulder 224 may restrict advancement of a jaw 202 into an alignment aperture 182 along a height axis 114, to set the elevation or depth of the jaw with respect to the height axis. In some embodiments, a single shoulder or stop region may be sufficient to set the elevation of both jaws. However, the presence of a shoulder or stop region for each jaw may more reliably and reproducibly ensure that the crimping tool (e.g., a proximal-distal axis defined by the tool) is orthogonal to the fastening member and/or crimp region, and/or with a compression axis 226 of tool 200 arranged substantially parallel to compression axis 95 of crimp region 92. The shoulder or stop region of the tool may engage any suitable portion of fastening member 70, generally top surface region 110, such as a top side of crimp region 92 adjacent contact site 184 and/or a border area of top surface region 110 adjacent any other suitable perimeter region of alignment aperture 182. Shoulder 224 may permit the jaw to advance through alignment aperture 182 to a position even with or below bottom surface region 112, as shown here. Prongs 150 may elevate bottom surface region 112 from bone (e.g., see FIG. 12), which may allow the jaws to project below bottom surface region 112.

Each jaw 202 may be configured to mate with alignment aperture 182 such that the position of the jaw is defined along compression axis 95 (and/or spanning axis 118). Accordingly, the jaw may be sized in correspondence with the alignment aperture along compression axis 95 (and/or spanning axis 118), such that the jaw fits closely into the alignment aperture.

Figure 16:
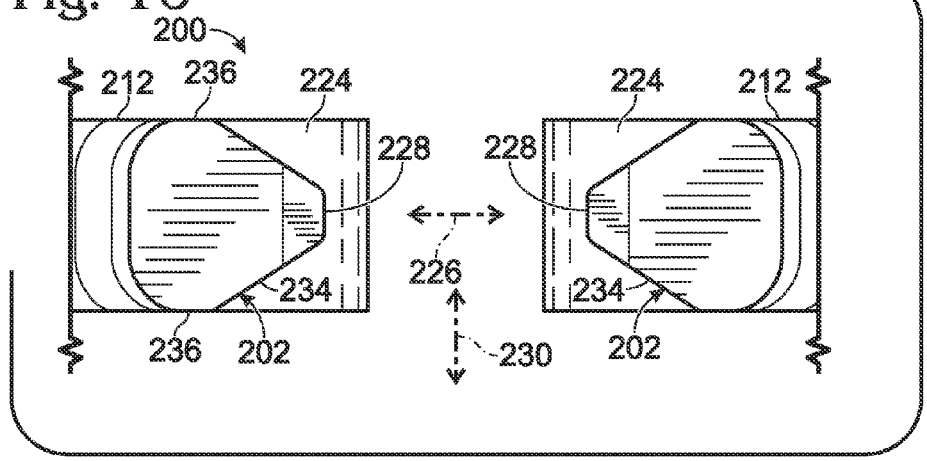
FIG. 16 is a distal end view of the jaws of the crimping tool of FIG. 14, taken generally along line 16-16 of FIG. 14, in accordance with aspects of the present disclosure.

FIG. 16 shows a distal end view of jaws 202 of tool 200, with the tool in the more open configuration (see FIG. 14). Jaws 202 may have opposing jaw faces 228 arranged orthogonal to compression axis 226 and/or facing each other. Each face 228 may be transversely convex (i.e., convex along a transverse axis 230 orthogonal to compression axis 226 and orthogonal to a proximal-distal axis 232 (optionally, a long axis) defined by tool 200; also see FIG. 14). Face 228 may be defined by a projecting region 234 of jaw 202 that tapers toward the other jaw. A tip portion of projecting region 234 may provide face 228.

Each jaw 202 may have opposing lateral side wall regions 236 that face away from each other. Side wall regions may be spaced from each other along transverse axis 230.

Figure 17:
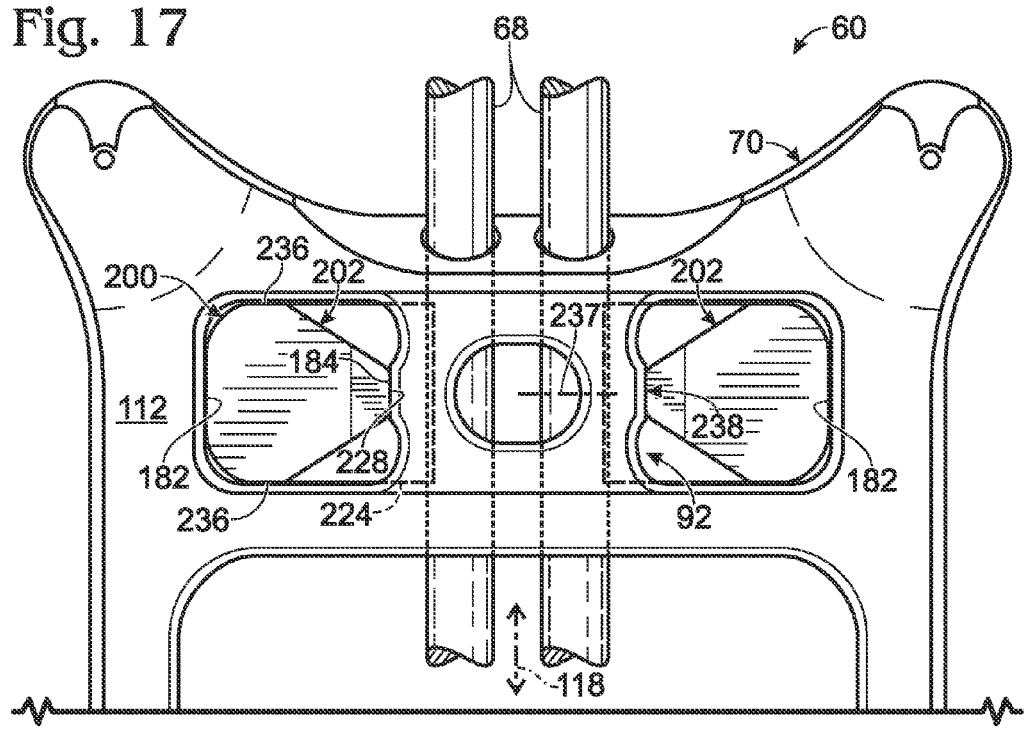
FIG. 17 is a fragmentary distal end view of the jaws of the crimping tool of FIG. 14, taken as in FIG. 16, with the jaws of the crimping tool mated with the binding device of FIG. 2 such that the jaws are aligned with a crimp region of the fastening member, and with binding device shown in a fragmentary view taken from below the fastening member, in accordance with aspects of the present disclosure.

FIG. 17 shows a distal end view of jaws 202 of crimping tool 200, with the jaws of the crimping tool mated with alignment apertures 182, as in FIG. 15, before fastening member 70 is crimped. The transverse dimension of each jaw, as measured between side wall regions 236, may correspond to the characteristic dimension of each guide aperture 182 measured parallel to spanning axis 118. Aperture 182 may guide a jaw to the crimp region such that the jaw is centered on the crimp region. For example, a plane 237 may extend orthogonally to spanning axis 118 through a central portion 238 of the crimp region, and the jaw may be guided to a position at which the jaw is centered about plane 237. The plane may conceptually divide the crimp region in half.

One or both lateral side wall regions 236 may contact corresponding side wall regions of alignment aperture 182 to center the jaw. In other embodiments, alignment aperture 182 may be wider than jaw 202, measured parallel to transverse axis 230, and the jaw may be centered by contact with only one side wall region of the guide aperture (e.g., see Example 2).

The crimping tool and fastening member may be configured to be mated in a predetermined arrangement that disposes compression axis 226 of tool 200 parallel to the compression axis of the fastening member, transverse axis 230 of the tool parallel to the spanning axis of the fastening member, and/or proximal-distal axis 232 of the tool parallel to a height axis of the fastening member (and/or orthogonal to a plane defined by the fastening member). In other words, alignment apertures 182 may be configured to align jaws of tool 200 with the crimp region.

III. Installation

This section describes exemplary methods of installing a bone binding system on bone; see FIGS. 18-21. The steps described in this section may be performed in any suitable order and combination and with any suitable devices having any suitable combination of features described in the present disclosure.

At least one bone may be selected for stabilization. The bone may be or include any suitable bone of a human or other vertebrate species. Exemplary bones that may be suitable include at least one bone of the arms (humerus, radius, and/or ulna), wrists (carpal), hands (metacarpal and/or phalange), legs (femur, tibia, and/or fibula), feet (talus, calcaneus, tarsal, metatarsal, and/or phalange), ribs, spine, pelvis, or cranium, or a sternum, clavicle, mandible, or scapula, among others. The bone selected may have a discontinuity (e.g., a cut, a fracture, a nonunion, or the like) or may be otherwise structurally compromised (e.g., osteoporotic bone).

One or more binding devices may be selected to stabilize the bone. Each binding device may include a fastening member and one or more encircling members.

The fastening member and the encircling member of the binding device may be assembled around a portion of bone. Assembly may include forming a loop. To form the loop, the encircling member may be disposed in one or more passages of the fastening member. For example, both free ends of the encircling member may be passed through respective passages of the fastening member from opposite sides of the fastening member. Alternatively, one end of the encircling member may be passed through a first passage of the fastening member and then the same free end may be passed through a second passage (or the first passage again) from the same side of the fastening member. In any event, after assembly, the encircling member may span the fastening member, and/or a crimp region thereof, twice (i.e., exactly or at least twice).

Assembling the binding device may include encircling a portion of the selected bone with the encircling member. For example, the encircling member may extend completely around a perimeter of the bone, or the encircling member may extend completely around only a portion of the bone that is bounded partly by a perimeter of the bone and partly by interior bone. In some embodiments, the encircling member may be connected to a curved needle that allows a surgeon to drive the encircling member through the bone, with the encircling member entering and exiting the bone at spaced positions, typically on the same side of the bone.

The fastening member may be placed on the bone. Placing the fastening member may cause the fastening member to span a discontinuity in the bone and may position one or more prongs of the fastening member on bone on opposite sides of the discontinuity. The fastening member may be placed on the bone (a) before the fastening member is assembled with the encircling member, (b) with the fastening member partially assembled with the encircling member (e.g., with the encircling member spanning a crimp region only once), or (c) by drawing the fastening member into position on bone, after the fastening member is assembled with the encircling member to form a loop, by decreasing the size of the loop.

FIG. 18 shows an exemplary arrangement of encircling member 68 and fastening member 70 that may be produced by assembling the members around sternum 52 (also see FIG. 2). The encircling member may span the fastening member twice to form loop 76. The loop may extend between aligned pairs of costal cartilages on both lateral sides of the sternum (i.e., with the loop generally orthogonal to the long axis of sternum 52) or may extend between offset pairs of costal cartilages (e.g., see Example 3). In some embodiments, the loop may extend through the sternum without extending between any pairs of costal cartilages (e.g., see FIG. 1).

In some embodiments, the fastening member may be assembled with a plurality of encircling members. Each pair of the encircling members may be arranged parallel or non-parallel (e.g., orthogonally or obliquely) to each other. The pair of encircling members may or may not cross each other. In some embodiments, two or more pairs of encircling members may be assembled with the fastening member with the members of each pair crossing each other but not crossing either member of the other pair.

Both free ends 78, 80 of encircling member 68 may be tensioned, indicated by tension arrows 82, 84. Tension may be applied with the free ends grasped manually and/or tension may be applied with a tensioning tool. For example, free ends 78, 80 may be attached to the tensioning tool before the tensioning tool is operated to increase tension on the encircling member. An exemplary tensioning tool that may be suitable is disclosed in U.S. Patent Application Publication No. 2011/0112537 A1, published May 12, 2011, which is incorporated herein by reference. The use of a tensioning tool may be advantageous because, in some cases, the tensioning tool can maintain tension on the encircling member while the encircling member is being secured (e.g., crimped). Tensioning the encircling member may compress bone, such as urging fragments 64, 66 of the sternum toward one another.

FIG. 19 shows binding device 60 after the fastening member has been crimped to attach loop ends 88, 90 of encircling member 68 to the fastening member (also see FIG. 3). The encircling member may be secured in a tensioned configuration that compresses the sternum. The fastening member may be crimped with any suitable tool capable of applying compression to the crimp region of the fastening member. For example, crimping tool 200 of FIGS. 14-17 may be used (see Section II).

FIG. 20 shows binding device 60 after opposing end pieces 240, 242 of the encircling member outside the loop have been cut off. Each end piece may be removed (e.g., moved away from the surgical site/subject), indicated by arrows at 244. Here, end piece 240 is created by cutting encircling member 68 in window 132, which leaves only loop 76 spanning window 132. Accordingly, if the binding device needs to be removed at a later time, for re-entry into the chest cavity, the surgeon can cut the span of the encircling member in the window without generating a separate piece that is not attached to the fastening member. In other embodiments, end piece 240 may be created by cutting encircling member 68 outside window 32, namely, to the left of fastening member 70 in FIG. 20.

FIG. 21 shows binding device 60 during a re-entry procedure to re-access the chest cavity. The loop of the encircling member has been cut within window 132, indicated by an arrow at 246, which sections the encircling member into two pieces, each of which is attached to the fastening member at the crimp region. After the loop is cut, a new end 248 of encircling member 68 can travel freely through channel 126. For example, the left side of fastening member 70 in FIG. 21 may be lifted upward (equivalent to FIG. 13), to slide the fastening member off new end 248. As another example, new end 248 may be pulled or pushed through channel 126 by manipulating the encircling member. In any event, after the loop has been cut, the fastening member and the encircling member may be separated from sternum 52.

Further aspects of installing binding devices of a cerclage system are described elsewhere in the present disclosure and in the references identified above under Cross-References, which are incorporated herein by reference.

IV. System Combinations

The device disclosed herein may be utilized and/or grouped in any suitable manner to provide a system, which may be supplied as a kit. The system (or kit) may include one or more fastening members and one or more encircling members. The system also or alternatively may include any combination of the following: a tensioning tool, a crimping tool, a cutting tool, and instructions for use. Each system component may be configured for single use (e.g., fastening and securing members) or for multiple use (e.g., the tools). Some or all of the components of the system (or kit) may be provided in a sterile condition, such as packaged in a sterile container.

V. Examples

The following examples describe selected aspects and embodiments of the present disclosure related to systems for binding bone. These examples are included for illustration and are not intended to limit or define the entire scope of the present disclosure.

Example 1

Fastening Member with Compact Geometry

This example describes an exemplary fastening member 270 that is a simplified version of fastening member 70 (e.g., FIGS. 2-5); see FIGS. 22 and 23.

Fastening member 270 may include spanning channels 128, 130 that extend through crimp region 92. Also, the fastening member may define alignment apertures 182 to receive jaws of a crimping tool. However, fastening member 270 may lack a cutting window. Also, the fastening member may or may not have prongs or other cleats projecting from the bottom surface region. The fastening member may be at least generally rectangular and may be elongated transverse to the spanning axis.

Example 2

Binding Device with Adjustable Prongs

Figure 24:
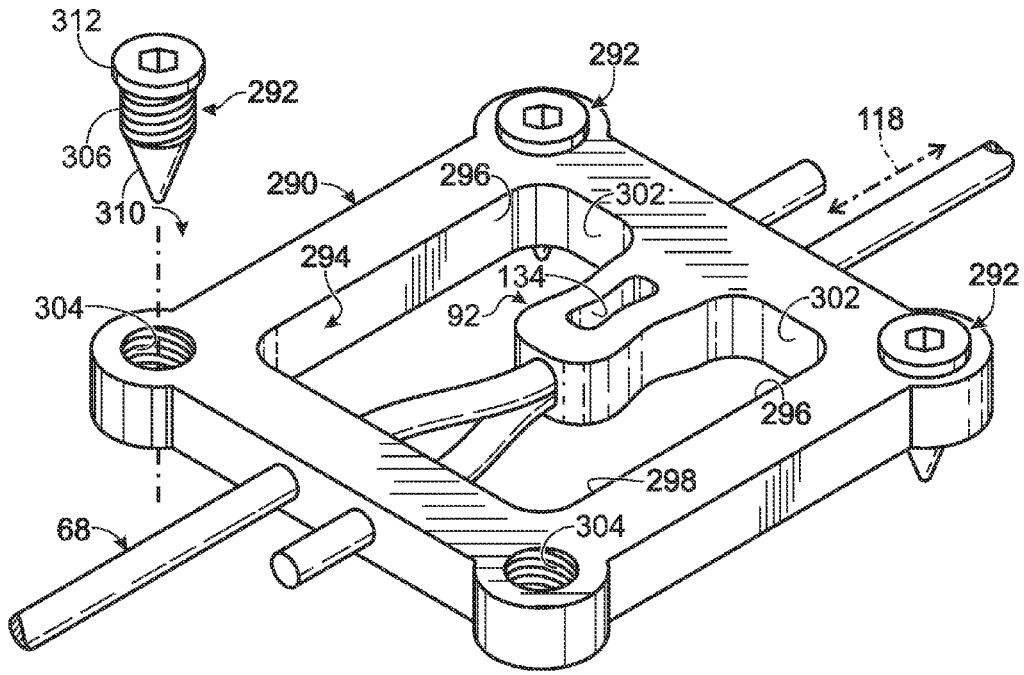
FIG. 24 is an isometric view of still another exemplary fastening member for the cerclage system of FIG. 1, with the fastening member configured to be attached to a plurality of adjustable prong members, one of which is shown exploded from the fastening member and a pair of which are shown in threaded engagement with the fastening member, in accordance with aspects of the present disclosure.
Figure 25:
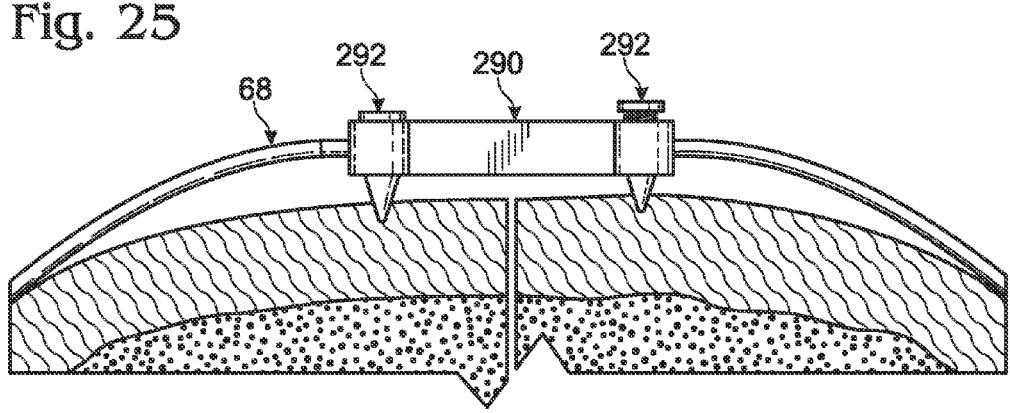
FIG. 25 is an elevational view of the fastening member of FIG. 24 attached to four prong members and securing an encircling member around a cut sternum, which is shown in cross-section, in accordance with aspects of the present disclosure.

This example describes an exemplary fastening member 290 capable of receiving a plurality of discrete prong members 292; see FIGS. 24 and 25.

Fastening member 290 may define an aperture 294 that functions as both an alignment aperture and a cutting window. Aperture 294 may be U-shaped to form a pair of alignment regions 296 and a window region 298. Jaws of a crimping tool may be received in alignment regions 296 to position the jaws for crimping a crimp region 92. The crimp region may have any suitable combination of the structure or features disclosed above for crimp region 92 of fastening member 70 (e.g., see FIGS. 2-5). Side wall regions 302 of alignment regions 296 may be abutted with the lateral side walls of the jaws, to center the jaws with respect to the crimp region (e.g., to determine the position of the jaws along spanning axis 118). The jaws of a cutting tool may be placed in window region 298 to cut encircling member 68.

Fastening member 290 may define apertures 304 to receive prong members 292. Each aperture may be configured for adjustable engagement with a prong member. For example, the aperture may define an internal thread, and the prong member may define a complementary external thread formed by a threaded region 306. The prong member may have a nonthreaded tip portion 310 that projects from the externally threaded region, optionally tapering away from the threaded region. The presence of a nonthreaded tip portion, instead of a threaded tip portion, may be advantageous for adjusting the position of the fastening member. For example, the length of the prong member projecting below the fastening member can be adjusting by turning the prong member, to either advance or retract the tip portion. Adjusting a prong member may change the amount by which the tip portion digs into bone. In some cases, since the tip portion does not thread into bone, changes in the length of the tip portion projecting below the fastening member can produce or adjust the size of a gap between the bottom surface region of the fastening member and the underlying surface region of bone, to change an elevation of the fastening member above bone. Advancing or retracting all or only a subset of the prong members can raise or lower the fastening member, to increase or decrease the separation between the fastening member and bone. In some cases, advancing one or more of the fastening members, to increase the elevation of at least a portion of the fastening member, can increase the tension on the encircling member loop, which may provide closure force to urge fragments of the sternum (or other bone) together. Alternatively, advancing or retracting the prong members (such as a subset of the prong members) can change the angle at which the fastening member (e.g., a plane defined by the fastening member) is oriented with respect to bone, which may increase or decrease a slant, if any, of the fastening member with respect to the adjacent surface region of bone. For example, adjusting the prong members can level the fastening member above bone (see FIG. 25).

Each prong member may have a stop structure, such as a head 312 or a thread run out, among others, that blocks advancement of the prong member through an aperture 304. In some cases, the prong member may be headless and, optionally, may be advanceable to a position where the prong member does not project above the top surface region of the fastening member (e.g., the proximal end of the prong member may be flush with or recessed with respect to the top surface region of the fastening member).

Any of the fastening members of the present disclosure may be equipped with one or more apertures 304 for discretionary use with one or more prong members 292. Each prong member may be attached to the fastening member by threaded engagement at any suitable time, such as before or after the fastening member is arranged with the encircling member to form a loop, and/or before or after the fastening member is crimped to attach the encircling member.

Example 3

Fastening Members Secured to Multiple Encircling Members

This example describes exemplary fastening members each configured to receive and secure two or more loops formed by two or more encircling members; see FIGS. 26-31.

Each fastening member may position at least a pair of encircling members on parallel, orthogonal, or oblique paths through the fastening member, around a portion of bone, and/or with respect to a long axis of a bone. Each pair of the encircling members may or may not cross each other. For example, the pair of encircling members each may extend on a path that is not orthogonal to the long axis of a bone, such that the members cross. In another example, a pair of encircling members may not cross because they are parallel or because they are nonparallel and sufficiently offset from each other along the bone. Each pair of encircling members may span the same window, distinct windows, or one or both may not span a window.

FIG. 26 shows an exemplary binding device 320 stabilizing a cut sternum 52 and including a fastening member 322 having a pair of transversely-arranged crimp regions 92 to secure a pair of discrete encircling members 68a, 68b around a portion of bone. Fastening member 322 may define a window 132 spanned by each encircling member 68a, 68b. The encircling members may be disposed in a crossed configuration in which respective loops 76a, 76b cross each other one or more times. For example, the encircling members may cross each other in window 132, indicated at 324, and at a second position on the opposite side (here, the posterior side) of sternum 52 (or other portion of bone). Each loop 76a and 76b may be arranged obliquely to a long axis 326 defined by sternum 52, with opposite sides of each loop having a different position along sternum 52. Here, the left side of loop 76a is positioned more superiorly than the right side and extends intermediate a different pair of costal cartilages on respective left and right sides of the sternum. Opposite sides of loop 76b also extend intermediate different pairs of costal cartilages with an inferior to superior orientation of the loop between left and right sides of the sternum.

Each encircling member 68a and 68b may span fastening member 322 and/or window 132 one or more times. For example, here, each encircling member extends twice through the corresponding crimp region 92 and only once across window 132. In some embodiments, each encircling member may be tensioned and the crimp region crimped with the encircling member spanning the fastening member twice (e.g., as in FIGS. 2, 18, and 19) and then an end of the encircling member may be truncated in window 132 to form stub 96.

Fastening member 322 may be modified to accommodate additional encircling members. For example, the fastening member may be elongated and configured to receive two or more pairs of encircling members secured with four or more crimp regions, with each encircling member spanning the same window of the fastening member. Each pair of encircling members may cross each other, and the distinct pairs may be arranged along the fastening member from each other. Members of one pair may or may not cross one or both members of the other pair.

In some embodiments, fastening member 322 may be modified to form two or more portions each defining a distinct window, with the portions arranged along a long axis of the fastening member. For example, the fastening member may have a pair of portions that collectively form a figure-eight shape. Each portion may be structured like fastening member 322 to receive a pair of encircling members in a crossing configuration, with each pair of encircling members not crossing either member of the other pair.

FIG. 27 shows an exemplary fastening member 340 configured to secure three copies of an encircling member. The fastening member may have a ring portion 342 providing top and bottom surface regions 110, 112. Prongs 150 may project downward from bottom surface region 112 and three pairs of passage members 344, 346 may project upward from top surface region 110. Passage member 344 provides crimp region 92. Passage member 346 may define one channel 348 or a pair of channels to receive the encircling member. The encircling member may be received one or more times in the channel or pair of channels. For example, channel 348 may be sized (shown in phantom outline) to receive the encircling member twice.

Ring portion 342 and the passage members collectively may define window 132. Each pair of passage members 344, 346 may receive and secure a distinct encircling member loop that spans the fastening member and/or window 132 one or more times. The loops may be arranged in a crossed configuration in the window and outside the fastening member on opposite sides of the bone, and at any suitable orientation with respect to bone. For example, two of the loops may be arranged generally as in FIG. 26, and a third loop may be oriented longitudinally with respect to the sternum or other bone.

FIG. 28 shows another fastening member 360 configured to secure a pair of encircling members extending around a portion of bone in a crossed configuration. The fastening member may have a pair of dedicated channels 362 or 364 for each encircling member. Channels 362 and channels 364 may be disposed at a different height above the bottom surface region of the fastening member or may be disposed at the same height. For example, here, channels 364 are disposed above channels 362, to avoid a channel intersection where the encircling members may interfere with one another. The fastening member may provide a distinct crimp region 366 for each channel, which allows the ends of each encircling-member loop to be secured independently to the fastening member. In other embodiments, the pair of crimp regions 366 for each encircling member may be replaced by a single crimp region, such as crimp region 92 of fastening member 70. Further aspects of structures and features that may be suitable for fastening member 360 are described in U.S. Patent Application Publication No. 2010/0094294 A1, published Apr. 15, 2010, which is incorporated herein by reference.

FIG. 29 shows a pair of exemplary binding devices 380 stabilizing cut sternum 52. Each device 380 includes a pair of encircling members 68 secured around a portion of the sternum in a parallel configuration, orthogonal to the long axis of the sternum, with a same fastening member 382. Each encircling member may or may not extend into the sternum.

Fastening member 382 defines a single window 132 spanned by each encircling member 68. Each encircling member is secured at a distinct crimp region 92. The fastening member has alignment apertures 182 that opposingly flank each crimp region. One of the alignment apertures may be shared by both crimp regions.

FIG. 30 shows a pair of exemplary binding devices 400 stabilizing cut sternum 52. Each device 400 includes a pair of encircling members 68 secured around a portion of the sternum in a parallel configuration with a same fastening member 402. Each encircling member may or may not extend into the sternum.

Fastening member 402 defines a pair of windows 132 each spanned by one of the encircling members. Each window may be open laterally (an open perimeter), as shown here, or may be completely bounded around its perimeter (a closed perimeter) (e.g., see FIGS. 2-5). Windows 132 may be open on opposite lateral sides of fastening member 402.

Each encircling member is secured at a distinct crimp region 92. An alignment aperture 182 may be shared by both crimp regions. To deform a crimp region, the jaws of a crimping tool may be placed on opposite sides of the crimp region, with one jaw disposed in aperture 182, and the other jaw abutted with a lateral wall region at the perimeter of the fastening member.

FIG. 31 shows a pair of exemplary binding devices 420 stabilizing cut sternum 52. Each device 420 includes a pair of encircling members 68 secured around a portion of the sternum in a parallel configuration, orthogonal to the long axis of the sternum, with a same fastening member 422. Each encircling member may or may not extend into the sternum. Fastening member 422 defines a U-shaped aperture 294 that functions as both a window for receiving jaws of a cutting tool and an alignment aperture for receiving jaws of a crimping tool (also see FIG. 24).

Example 4

Fastening Member with Perimeter Cutting Windows

Figure 32:
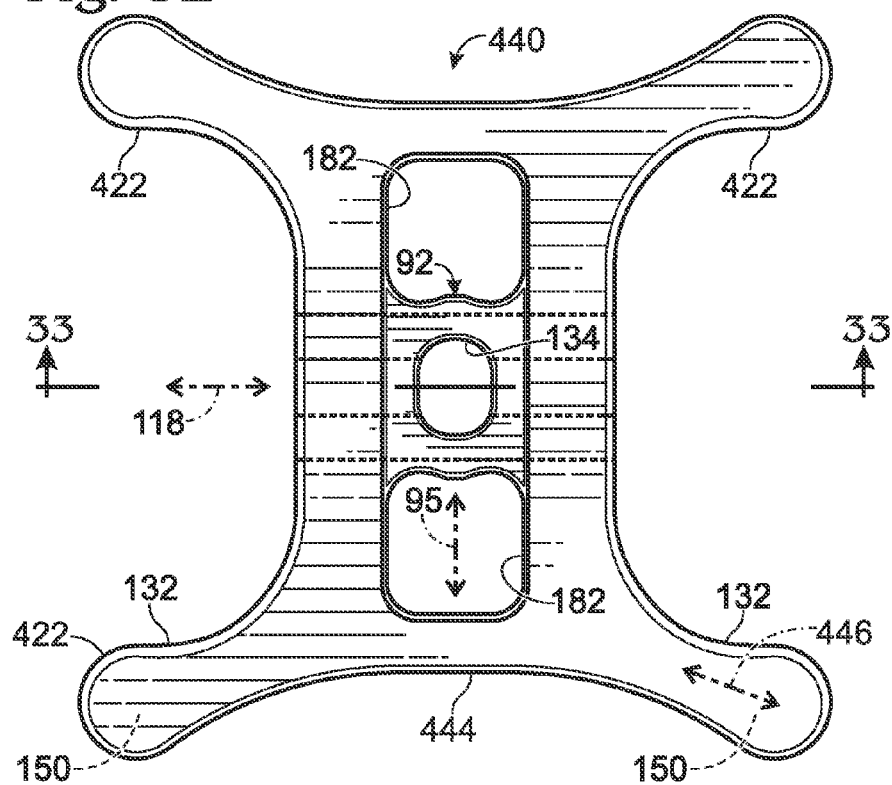
FIG. 32 is a plan view of an exemplary fastening member for a binding device and including two pairs of elongate tabs, with each pair bounding opposite sides of a distinct, unenclosed window defined by the fastening member, in accordance with aspects of the present disclosure.
Figure 33:
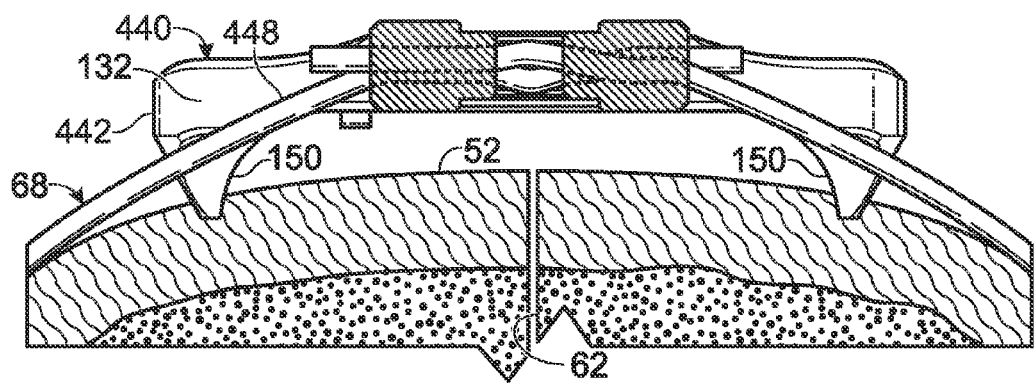
FIG. 33 is a sectional view of the fastening member of FIG. 32, taken generally along line 33-33 of FIG. 32, with the fastening member securing an encircling member to a cut sternum, in accordance with aspects of the present disclosure.

This example describes an exemplary binding device including a fastening member 440 with elongate tabs or protrusions 442 that opposingly flank a pair of perimeter cutting windows 132; see FIGS. 32 and 33. Tabs 442 each may be equipped with a prong 150 formed under and projecting downward from each tab.

Each tab 442 may be structured as an elongated corner of the fastening member. The tab may project from a body portion 444 that provides crimp region 92. The tab may project along an axis 446 that is parallel or oblique to spanning axis 118 of the fastening member. For example, axis 446 may form a smaller angle with spanning axis 118 than with crimping axis 95. A characteristic dimension of the fastening member and/or of a tab, measured parallel to spanning axis 118 may be at least about twice a characteristic dimension of body portion 444, measured parallel to the same axis.

FIG. 33 shows fastening member 440 disposed on sternum 52 and securing encircling member 68 to the sternum. Tabs 442 in combination with prongs 150 may elevate a region 448 of the encircling member that extends out of window 132 toward bone. The elevated region of the encircling member may be conveniently positioned in window 132 for cutting the encircling member in a re-entry procedure.

Example 5

Crimping a Fastening Member Using Male and Female Jaws

This example describes use of an exemplary crimping tool 460 having opposable jaws 462, 464 providing jaw faces that are respectively convex and concave; see FIGS. 34-36.

FIG. 34 shows an exemplary binding device 470 in an assembled configuration before crimping with tool 460 (see FIGS. 35 and 36). Device 470 includes fastening member 472 and encircling member 68 that spans crimp region 92 twice.

Crimp region may include a plurality of deformable apertures 134, which may be arranged along or transverse to spanning axis 118 from each other. Alignment apertures 182 may be bounded by contact sites 184 that are linear, as shown here, or convex and/or concave.

FIG. 35 shows crimping tool 460 mated with fastening member 472, with male jaw 462 and female jaw 464 received in respective alignment apertures 182. Male jaw 462 may have a jaw face defining a protrusion 474 that is aligned, along spanning axis 118, with a recess 476 defined by the jaw face of female jaw 464.

FIG. 36 shows how jaws 462, 464 can deform crimp region 92 when the jaws apply compressive force, indicated by arrows at 478, to the opposing contact sites of the crimp region. The male jaw may form an indentation 480 in the adjacent contact site of the crimp region. The female jaw may form a protrusion 482 in the adjacent contact site of the crimp region, with protrusion 482 aligned with indentation 480. In some cases, the female jaw also may form one or more indentations 484 in the adjacent contact site of the crimp region.

Example 6

Selected Embodiments

This example describes selected embodiments of the present disclosure, presented as a series of numbered paragraphs.

A1. A method of binding bone, the method comprising: (a) selecting a fastening member having a crimp region and defining a window at least partially bounded by a wall region of the fastening member; (b) arranging an encircling member to extend through the crimp region and form a loop around a portion of bone and span the window outside the crimp region between spaced sites of the wall region; and (c) crimping the crimp region to secure at least one end of the loop to the fastening member.

A2. The method of paragraph A1, further comprising a step of sectioning the encircling member with a cut placed through a portion of the encircling member that spans the window.

A3. The method of paragraph A2, wherein the step of sectioning the encircling member is performed with a cutting tool disposed in the window.

A4. The method of paragraph A2, wherein the step of sectioning the encircling member includes a step of cutting the loop after the step of crimping.

A5. The method of paragraph A2, wherein the step of sectioning the encircling member includes a step of cutting through the encircling member at a position outside the loop.

A6. The method of paragraph A5, wherein the step of sectioning the encircling member cuts through the encircling member at a first position along the loop and at a second position outside the loop.

A7. The method of paragraph A1, wherein the step of arranging includes a step of arranging the fastening member such that a top surface region of the fastening member faces away from the portion of bone and a bottom surface region of the fastening member faces toward the portion of bone.

A8. The method of paragraph A7, wherein the step of arranging includes a step of arranging the encircling member such that both ends of the loop extend through the fastening member on a path intermediate the top and bottom surface regions.

A9. The method of paragraph A1, wherein the step of arranging exposes a portion of the encircling member in the window.

A10. The method of paragraph A1, wherein the fastening member has a bottom surface region that faces bone, and wherein the step of arranging positions the encircling member such that the encircling member is elevated from the bottom surface region at each of the spaced sites of the wall region.

A11. The method of paragraph A1, wherein the step of arranging causes the encircling member to span the window of the fastening member twice.

A12. The method of paragraph A1, wherein the window has a closed perimeter.

A13. The method of paragraph A1, wherein the step of crimping does not substantially change the shape of the window.

A14. The method of paragraph A1, wherein the encircling member includes a wire, a cable, or both.

A15. The method of paragraph A1, wherein the window is U-shaped.

A16. The method of paragraph A1, wherein the fastening member has a pair of crimp regions, and wherein the steps of arranging and crimping are performed with a pair of encircling members each secured by a distinct crimp region.

A17. The method of paragraph A16, wherein the pair of encircling members form a pair of loops that are parallel to each other.

A18. The method of paragraph A16, wherein the pair of encircling members form a pair of loops that orthogonal or oblique to each other.

A19. The method of paragraph A18, wherein the pair of loops cross each other in the window.

A20. The method of paragraph A18, wherein the pair of loops do not cross each other in the window.

A21. The method of paragraph A16, wherein each of the encircling members spans the window.

A22. The method of paragraph A16, wherein the fastening member has a pair of windows, and wherein each of the encircling members spans a distinct window of the pair of windows.

A23. The method of paragraph A1, further comprising a step of disposing each of one or more prong members in threaded engagement with the fastening member and non-threaded engagement with the bone.

B1. A system for binding bone, comprising: (a) a surgical encircling member; and (b) a fastening member having a crimp region and defining a window at least partially bounded by a wall region of the fastening member, the fastening member being configured to form an arrangement with the encircling member in which the encircling member extends through the crimp region twice and forms a loop around a portion of bone with the loop spanning the window outside the crimp region between spaced sites of the wall region, the crimp region being configured to be crimped such that both ends of the loop are secured to the fastening member.

B2. The system of paragraph B1, further comprising a cutting tool capable of sectioning the encircling member with a cut placed through a portion of the encircling member that spans the window.

B3. The system of paragraph B1, wherein the cutting tool has a pair of jaws capable of being operatively disposed in the window for sectioning the encircling member.

B4. The system of paragraph B1, wherein the fastening member has a top surface region opposite a bottom surface region and defines a path for the encircling member to extend through the fastening member intermediate the top and bottom surface regions.

B5. The system of paragraph B1, wherein a region of the encircling member that spans the window is exposed in the window.

B6. The system of paragraph B1, wherein the fastening member has a bottom surface region configured to face bone, and wherein the encircling member is elevated from the bottom surface region at each of the spaced sites.

B7. The system of paragraph B1, wherein the window has a closed perimeter.

B8. The system of paragraph B1, wherein the surgical encircling member includes a wire, a cable, or both.

B9. The system of paragraph B1, wherein the fastening member already has been assembled with the encircling member such that the encircling member extends twice through the crimp region to form the loop and spans the window outside the crimp region between the spaced sites of the wall region, and wherein the crimp region has been crimped such that both ends of the loop are secured to the fastening member.

B10. The system of paragraph B1, wherein the fastening member has a pair of crimp regions configured to secure a pair of loops formed by one or more encircling members.

B11. The system of paragraph B10, wherein the pair of crimp regions are arranged parallel to each other.

B12. The system of paragraph B10, wherein the pair of crimp regions are arranged obliquely or orthogonally to each other.

B13. The system of paragraph B12, wherein the fastening member is configured to position the pair of loops in a crossing configuration in which the pair of loops cross one another in the window of the fastening member.

B14. The system of paragraph B12, wherein the fastening member is configured to position the pair of loops in a noncrossing configuration such that the pair of loops do not cross one another in the window of the fastening member.

B15. The system of paragraph B10, wherein the fastening member is configured to position the pair of loops such that both loops span the same window of the fastening member.

B16. The system of paragraph B10, wherein the fastening member has a pair of windows and is configured to receive the encircling members such that each loop spans a distinct window of the pair of windows.

B17. The system of paragraph B1, wherein the fastening member defines a plurality of apertures, further comprising a plurality of prong members configured to the received in the plurality of apertures, in threaded engagement with the fastening member, with a tip portion of each prong member projecting an adjustable distance from the fastening member for nonthreaded engagement with the bone.

B18. The system of paragraph B1, further comprising a tool having a pair of jaws to crimp the crimp region, wherein the fastening member defines an aperture configured to guide the jaw to the crimp region.

B19. The system of paragraph B18, wherein the encircling member extends through the crimp region on a path parallel to a spanning axis, and wherein the aperture is configured to guide the jaw of the tool to a position on the crimp region such that the jaw is centered about a plane that is orthogonal to the spanning axis and that extends through a central portion of the crimp region.

B20. The system of paragraph B19, wherein the plane conceptually divides the crimp region into two halves arranged along the spanning axis from each other.

B21. The system of paragraph B18, wherein the encircling member extends through the crimp region on a path parallel to a spanning axis, and wherein the aperture is configured to guide the jaw to a predefined position along a line parallel to the spanning axis.

B22. The system of paragraph B1, further comprising a crimping tool having a pair of jaws to crimp the crimp region and a stop region configured to contact the fastening member to block advancement of at least one of the jaws through the aperture and set an elevation of the at least one jaw for crimping the crimp region.

B23. The system of paragraph B1, wherein the stop region is formed as a shoulder on a jaw of the tool.

B24. The system of paragraph B1, wherein the window has an area that is at least one-fourth of an area enclosed by a perimeter of the fastening member.

C1. A method of binding bone, the method comprising: (a) arranging an encircling member to extend twice through a crimp region of a fastening member and form a loop around a portion of bone; (b) guiding a jaw of a tool to the crimp region with an aperture of the fastening member; and (c) crimping the crimp region of the fastening member with the tool to secure both ends of the loop to the fastening member.

C2. The method of paragraph C1, wherein the encircling member extends through the crimp region on a path parallel to a spanning axis, and wherein the step of guiding guides the jaw such that the jaw is centered about a plane that is orthogonal to the spanning axis and that extends through a central portion of the crimp region.

C3. The method of paragraph C2, wherein the plane conceptually divides the crimp region into two halves arranged along the spanning axis from each other.

C4. The method of paragraph C1, wherein the step of guiding includes a step of contacting the jaw with a wall region bounding a portion of the aperture and extending transverse to the spanning axis.

C5. The method of paragraph C1, wherein the jaw has a face region to contact the crimp region and lateral sides disposed opposite each other and transverse to the face region, and wherein the aperture has a wall region that contacts a lateral side of the jaw during the step of guiding.

C6. The method of paragraph C1, wherein the tool has a pair of jaws, and wherein the step of guiding includes a step of disposing the jaws in one or more apertures defined by the fastening member such that an aperture of the fastening member guides each of the jaws to the crimp region.

C7. The method of paragraph C6, wherein a distinct aperture guides each jaw to the crimp region.

C8. The method of paragraph C1, wherein the jaw is sized in correspondence with the aperture.

C9. The method of paragraph C1, wherein the jaw is shaped in correspondence with the aperture.

C10. The method of paragraph C1, wherein the tool has a pair of jaws and a stop region configured to contact the fastening member to block advancement of at least one jaw into the aperture to set an elevation of the at least one jaw for crimping the fastening member.

C11. The method of paragraph C10, wherein the stop region is in contact with the fastening member before and/or during the step of crimping.

C12. The method of paragraph C10, wherein the stop region is formed as a shoulder on a jaw of the tool.

D1. A system for binding bone, comprising: (a) a surgical encircling member; and (b) a fastening member having a crimp region and configured to form an arrangement with the encircling member in which the encircling member extends twice through the crimp region and forms a loop around a portion of bone, the fastening member defining an aperture configured to guide a jaw of a tool to the crimp region, the crimp region being configured to be crimped by the tool such that both ends of the loop are secured to the fastening member.

E1. A method of binding bone, the method comprising: (a) arranging a first encircling member and a second encircling member such that each encircling member extends twice through a fastening member to form respective first and second loops each extending around a portion of bone, the loops crossing one another; and (b) crimping the fastening member such that both ends of each loop are secured to the fastening member.

E2. The method of paragraph E1, wherein the bone is provided by a sternum, and wherein each loop is oriented obliquely with respect to the sternum.

E3. The method of paragraph E1, wherein each loop extends between a first pair of costal cartilages and a second pair of costal cartilages on opposite sides of the sternum, and wherein the first pair of costal cartilages is offset from the second pair of costal cartilages in a superior or inferior direction.

E4. The method of paragraph E1, wherein the loops cross one another adjacent a posterior surface region of the sternum, within the sternum, or both.

E5. The method of paragraph E1, wherein the loops cross one other in a same window defined by the fastening member.

E6. The method of paragraph E1, wherein the loops cross one another twice.

E7. The method of paragraph E1, wherein the fastening member has a pair of crimp regions configured to secure the first and second loops to the fastening member.

E8. The method of paragraph E7, wherein the pair of crimp regions are arranged parallel to each other.

E9. The method of paragraph E7, wherein the pair of crimp regions are arranged obliquely or orthogonally to each other.

E10. The method of paragraph E1, wherein the first and second loops are positioned in a crossing configuration in which the loops cross one another in a window defined by the fastening member.

E11. The method of paragraph E1, wherein the first and second loops are positioned in a non-crossing configuration such that the loops do not cross one another.

E12. The method of paragraph E1, wherein both loops span a same window defined by the fastening member.

E13. The method of paragraph E1, wherein the fastening member has a pair of windows and wherein each loop spans a distinct window of the pair of windows.

F1. A system for binding bone, comprising: (a) a surgical encircling member; (b) a fastening member having a crimp region and arrangeable with the encircling member such that the encircling member extends twice through the crimp region to form a loop around a portion of bone; and (c) a tool having a pair of jaws to crimp the crimp region, wherein the fastening member defines an aperture configured to guide a jaw of the tool to the crimp region.

F2. The system of paragraph F1, wherein the encircling member extends through the crimp region on paths parallel to a spanning axis, and wherein the jaw after being guided to the crimp region is centered about a plane, the plane being orthogonal to the spanning axis and extending through a central portion of the crimp region.

F3. The system of paragraph F1, wherein the aperture has a wall region bounding a portion of the aperture and extending transverse to the spanning axis, and wherein the wall region is configured to contact the jaw to guide the jaw to the crimp region.

F4. The system of paragraph F1, wherein the jaw has a face to contact the crimp region and lateral sides disposed opposite each other and transverse to the face, and wherein the aperture has a wall region configured to contact a lateral side of the jaw to guide the jaw to the crimp region.

F5. The system of paragraph F1, wherein the fastening member defines one or more apertures to receive both jaws such that an aperture guides each jaw to the crimp region.

F6. The system of paragraph F5, wherein the one or more apertures are a pair of discrete apertures.

F7. The system of paragraph F2, wherein the jaw has a face to contact the crimp region and lateral sides disposed opposite each other and transverse to the face, and wherein a width of the jaw measured between the lateral sides corresponds to a dimension of the aperture measured parallel to the spanning axis.

F8. The system of paragraph F1, wherein the tool has a stop region configured to contact the fastening member to set an elevation of at least one of the jaws for crimping the fastening member.

F9. The system of paragraph F8, wherein the stop region is a shoulder projecting from the jaw.

G1. A method of binding bone, the method comprising: (a) arranging an encircling member and a fastening member such that the encircling extends twice through the fastening member and forms a loop around a portion of bone; (b) crimping the fastening member such that both ends of the loop are secured to the fastening member; and (c) disposing each of one or more prong members in threaded engagement with the fastening member and nonthreaded engagement with the bone.

G2. The method of paragraph G1, further comprising a step of turning one of the prong members after the step of disposing to adjust a length of a nonthreaded portion of the prong member extending below a bottom surface region of the fastening member and a depth of the one prong member in the bone.

G3. The method of paragraph G1, further comprising a step of turning one of the prong members after the step of disposing to adjust a length of a portion of the prong member extending below a bottom surface region of the fastening member, such that a position of the fastening member relative to the bone is changed.

G4. The method of paragraph G3, wherein the step of turning increases the length of the portion of the prong member extending below the bottom surface region of the fastening member and urges at least part of the fastening member away from the bone.

G5. The method of paragraph G3, wherein the step of turning is performed after the step of crimping and increases a tension of the loop.

G6. The method of paragraph G3, wherein the step of turning is performed before the step of crimping and adjusts a slope of the fastening member with respect to the bone.

G7. The method of paragraph G1, wherein the step of disposing is performed before the step of crimping.

G8. The method of paragraph G1, wherein the step of disposing includes a step of disposing three or more prong members.

G9. The method of paragraph G8, wherein the step of disposing includes a step of disposing four prong members adjacent four respective corners of the fastening member.

G10. The method of paragraph G9, wherein each respective corner is formed by a tab projecting from a body of the fastening member.

H1. A method of binding bone, the method comprising: (a) arranging an encircling member such that the encircling member extends twice through a fastening member to form a loop around a portion of bone; (b) crimping the fastening member with a tool such that both ends of the loop are secured to the fastening member, wherein the tool has a pair of jaws and a stop region configured to contact the fastening member to block advancement of at least one of the jaws into the aperture to set an elevation of the at least one for crimping the fastening member.

H2. The method of paragraph H1, wherein the stop region is in contact with the fastening member before and/or during the step of crimping.

H3. The method of paragraph H1, wherein the stop region is formed as a shoulder on a jaw of the tool.

H4. The method of paragraph H1, wherein the fastening member has a top surface region, and wherein the stop region contacts the top surface region to set the elevation.

H5. The method of paragraph H1, wherein each jaw has a stop region configured to set a respective elevation of the jaw.

H6. The method of paragraph H1, wherein the fastening member defines an aperture to receive the at least one jaw, and wherein the stop region stops advancement of the at least one jaw through the aperture.

H7. The method of paragraph H1, wherein the fastening member defines a plane and the tool defines a proximal-distal axis, and wherein contact of the stop region with the fastening member is configured to orient the proximal-distal axis with respect to the plane.

H8. The method of paragraph H7, wherein the fastening member defines at least one aperture, further comprising a step of mating the at least one jaw with the at least one aperture such that the proximal-distal axis of the tool is orthogonal to the plane defined by the fastening member.

H9. The method of paragraph H1, wherein the fastening member defines a pair of apertures, further comprising a step of mating the tool with the fastening member such that each jaw is disposed in one of the apertures during the step of crimping.

I1. A system for binding bone, comprising: (a) a surgical encircling member; (b) a fastening member configured to be arranged with the encircling member such that the encircling member extends through the fastening member twice to form a loop around a portion of bone; and (c) a tool configured to crimp the fastening member such that both ends of the loop are secured to the fastening member, the tool having a pair of jaws and a stop region configured to contact the fastening member to block advancement of at least one of the jaws to set an elevation of the at least one jaw for crimping the fastening member.

I2. The system of paragraph I1, wherein the stop region is fixed to one of the jaws.

I3. The system of paragraph I1, wherein each jaw has a stop region that sets the respective elevation of the jaw.

I4. The system of paragraph I1, wherein the stop region is formed as a shoulder on one of the jaws.

I5. The system of paragraph I1, wherein the fastening member defines a spanning axis along which the encircling member is configured to extend into the fastening member, and wherein contact between the stop region and the fastening member is configured to establish an orientation of at least one jaw about a line parallel to the spanning axis.

I6. The system of paragraph I1, wherein the fastening member defines an aperture to receive the at least one jaw, and wherein the stop region is configured to stop advancement of the at least one jaw through the aperture.

I7. The system of paragraph I1, wherein the fastening member defines a plane and the tool defines a proximal-distal axis, and wherein contact of the stop region with the fastening member is configured to orient the proximal-distal axis with respect to the plane.

I8. The system of paragraph I7, wherein the fastening member defines at least one aperture, and wherein the at least one jaw is configured to be mated with the at least one aperture such that the proximal-distal axis of the tool is orthogonal to the plane defined by the fastening member.

I9. The system of paragraph I1, wherein the fastening member defines a pair of apertures, and wherein the tool is configured to be mated with the pair of apertures such that each jaw is disposed in one of the apertures.

J1. A method of binding bone, the method comprising: (a) selecting a fastening member having a side wall region defining a perimeter of the fastening member; (b) arranging an encircling member and the fastening member such that the encircling member extends twice through the fastening member from a first site to a second site of the side wall region to form a loop around a portion of bone, the side wall region being chamfered at the first and second sites to form respective overhangs; and (c) crimping the crimp region such that both ends of the loop are secured to the fastening member.

K1. A system for binding bone, comprising: (a) a surgical encircling member; and (b) a fastening member having a top surface region opposite a bottom surface region and a side wall region defining a perimeter of the fastening member, the fastening member defining one or more passages configured to receive the encircling member such that the encircling member extends twice through the fastening member from a first site to a second site of the side wall region to form a loop around a portion of bone, the side wall region being chamfered at the first and second sites such that the first and second sites slope convergently as each site extends toward the bottom surface region, the fastening member being configured to be crimped such that both ends of the loop are secured to the fastening member.

K2. The system of paragraph K1, wherein the first and second sites are present on opposite sides of the fastening member.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of binding bone, the method comprising:
    selecting a fastening member having a crimp region, the fastening member further defining a window bounded by wall regions of the fastening member;
    arranging an encircling member to extend twice through the crimp region and form a loop around a portion of bone, wherein the encircling member extends through the crimp region and then spans the window outside the crimp region, the window providing access to cut the encircling member; and
    crimping the crimp region to secure both ends of the loop to the fastening member.

2. The method of claim 1, further comprising a step of cutting the encircling member inside the window.

3. The method of claim 1, wherein the step of arranging exposes a portion of the encircling member in the window.

4. The method of claim 1, wherein the step of arranging causes the encircling member to span the window of the fastening member twice.

5. The method of claim 1, wherein the window has a closed perimeter.

6. The method of claim 1, wherein the step of crimping does not substantially change the shape of the window.

7. The method of claim 1, wherein the encircling member includes a wire or a cable.

8. The method of claim 1, wherein the fastening member has a pair of crimp regions, and wherein the steps of arranging and crimping are performed with a pair of encircling members such that each encircling member is associated with and secured by a different crimp region of the pair of crimp regions.

9. The method of claim 8, wherein the pair of encircling members form a pair of loops that are parallel to each other.

10. The method of claim 8, wherein the pair of encircling members form a pair of loops that cross each other.

11. The method of claim 10, wherein the pair of loops cross each other in the window.

12. The method of claim 1, further comprising a step of disposing each of one or more prong members in threaded engagement with the fastening member and nonthreaded engagement with the bone.

13. A method of binding bone, the method comprising:
arranging an encircling member to extend twice through a crimp region of a fastening member and form a loop around a portion of bone;
placing a jaw of a tool into an aperture of the fastening member, wherein the aperture is located adjacent the crimp region, and wherein the tool has a stop region configured to contact the fastening member to restrict advancement of the jaw into the aperture to set an elevation of the jaw for crimping the fastening member; and
crimping the crimp region of the fastening member with the tool to secure both ends of the loop to the fastening member.

14. The method of claim 13, wherein the encircling member extends through the crimp region on a path, and wherein the step of placing positions the jaw such that the jaw is centered about a plane that is orthogonal to the path and that extends through a central portion of the crimp region.

15. The method of claim 14, wherein the plane conceptually divides the crimp region into two halves arranged along the path from each other.

16. The method of claim 13, wherein the step of placing includes a step of contacting the jaw with a wall region bounding the aperture and extending transverse to the path.

17. The method of claim 13, wherein the jaw has a face to contact the crimp region and lateral sides disposed opposite each other and transverse to the face, and wherein the aperture has a wall region that contacts a lateral side of the jaw during the step of placing.

18. The method of claim 13, wherein the tool has a pair of jaws, wherein the fastening member defines a pair of apertures, and wherein the step of placing positions each of the jaws in a different aperture of the pair of apertures.

19. The method of claim 13, wherein the jaw is sized for placement in the aperture.

20. The method of claim 13, wherein the stop region is formed as a shoulder on the jaw.

21. The method of claim 13, wherein the encircling member extends through the crimp region along a path, and wherein the aperture is configured to guide the jaw to a predefined position along an axis parallel to the path.

22. A method of binding bone, the method comprising:
arranging an encircling member to extend twice through a crimp region of a fastening member and form a loop around a portion of bone, wherein the fastening member includes a plate member having a top surface and a bottom surface, wherein the fastening member defines a pair of apertures, and wherein each aperture extends through the plate member from the top surface to the bottom surface is defined by a closed periphery;
placing a pair of jaws of a tool into the pair of apertures such that each jaw is in a different aperture of the pair of apertures; and
crimping the crimp region of the fastening member with the tool while the pair of jaws remain in the pair of apertures, to secure both ends of the loop to the fastening member.

* * * * *